United States Patent
Ernst et al.

(10) Patent No.: US 6,479,424 B1
(45) Date of Patent: Nov. 12, 2002

(54) FLUXIONAL CATALYSTS AND RELATED LIGANDS CONTAINING BULKY SUBSTITUENTS

(75) Inventors: Andreas B. Ernst, Alpharetta, GA (US); Eric J. Moore, Wheaton, IL (US); Charles L. Myers, Palatine, IL (US); Roger W. Quan, Vernon Hills, IL (US)

(73) Assignee: BP Corporation North America Inc., Chicago, IL (US)

( * ) Notice: Subject to any disclaimer, the term of this patent is extended or adjusted under 35 U.S.C. 154(b) by 0 days.

(21) Appl. No.: 09/459,732

(22) Filed: Dec. 13, 1999

Related U.S. Application Data

(60) Provisional application No. 60/112,383, filed on Dec. 14, 1998.

(51) Int. Cl.[7] .............................. B01J 31/38; C08F 4/44
(52) U.S. Cl. ...................... 502/152; 502/117; 556/53; 526/160; 526/943; 526/351
(58) Field of Search ................................. 526/160, 943, 526/348.6, 351; 502/104, 117, 118, 152; 556/53, 11

(56) References Cited

U.S. PATENT DOCUMENTS

| | | | |
|---|---|---|---|
| 5,206,197 A | 4/1993 | Campbell, Jr. ............... | 502/103 |
| 5,491,246 A | 2/1996 | Rosen et al. .................... | 556/7 |
| 5,527,929 A | 6/1996 | Timmers et al. ................ | 556/7 |
| 5,594,080 A | 1/1997 | Waymouth et al. ........... | 526/126 |
| 5,616,748 A | 4/1997 | Newman ..................... | 556/11 |
| 5,886,117 A | 3/1999 | Campbell, Jr. ............... | 526/134 |
| 5,948,869 A | 9/1999 | Vallieri et al. ............... | 525/940 |
| 5,969,070 A | 10/1999 | Waymouth et al. .......... | 526/351 |
| 6,107,431 A | * 11/2000 | Resconi et al. ............. | 526/351 |

FOREIGN PATENT DOCUMENTS

| | | |
|---|---|---|
| EP | 421659 | 4/1991 |
| EP | 440014 | 8/1991 |
| EP | 492282 | 7/1992 |
| EP | 493678 | 7/1992 |
| EP | 505890 | 9/1992 |
| EP | 554574 | 8/1993 |
| EP | 570932 | 11/1993 |
| WO | 9620225 | 4/1996 |
| WO | WO 9712920 | 4/1997 |
| WO | 9857996 | 12/1998 |
| WO | WO 9946270 | 9/1999 |

OTHER PUBLICATIONS

"Addition of Aryl and Fluoroalkyl Radicals to Fullerene $C_{70}$: ESR Detection of Five Regioisomeric Adducts and Density Functional Calculations" J. Am. Chem. Soc. 1996, 118, 7608–7617.

Chen and Marks, "Cocatalysts for Metal–Catalyzed Olefin Polymerization: Activators, Activation Processes, and Structure–Activity Relationships," Chem. Rev. 2000, 100, pp. 1391–1434.

Ittel et al., "Late–Metal Catalysts for Ethylene Homo–and Copolymerization," Chem.Rev. 2000, 100, pp. 1169–1203.

Baird, "Carbocationic Alkene Polymerizations Initiated by Organotrasition Metal Complexes: An Alternative, Unusual Role for Soluble Ziegler–Natta Catalysts," Chem. Rev. 2000, 100, pp. 1471–1478.

Boffa and Novak, "Copolymerization of Polar Monomers with Olefins Using Transition–Metal Complexes," Chem. Rev. 2000, 100, pp. 1479–1493.

Chen et al., "Sterically Encumbered (Perfluoroaryl) Borane and Aluminate Cocatalysts for Tuning Cation–Anion Pair Structure and Reactivity in Metallocene Polymerizations Processes," J.Am.Chem.Soc. 1998, 120, pp. 6287–6305.

Soga et al., "Stereospecific Polymerization of Methyl Methacrylate Initiated by Dimethylzirconocene/$B(C_6F_5)_3$ or $Ph_3CB(C_6F_5)_4/Zn(C_2H_5)_2$," Macromolecules, 1994, 27, pp. 7938–7940.

Grassi et al., "Syndiotactic Styrene Polymerization Promoted by Half–Titanocene Catalysts: A Kinetic Investigation Providing a Closer Insight to the Active Species," Macromolecules, 1997, 30, pp. 1884–1889.

Duncalf et al., "Synthesis and Mechanism of Formation of Syndiotactic Polystyrene Using a (tert–Butylcyclopentadienyl)titanium Complex," Macromolecules, 1996, 26, pp. 6399–6403.

Heffner et al., "Two–Dimensional $^1H$ and $^{13}C$ NMR Spectroscopy of Styrene–Methyl Methacrylate Copolymers," Macromolecules, 1986, 19, pp. 1628–1634.

Bovey, "Polymer NMR Spectroscopy. VI. Methyl Methacrylate–Styrene and Methyl Methacrylate–α–Methylstyrene Copolymers," J. of Poly. Sci., 62, pp. 197–209 (1962).

(List continued on next page.)

Primary Examiner—David W. Wu
Assistant Examiner—R. Harlan
(74) Attorney, Agent, or Firm—Wallace L. Oliver

(57) ABSTRACT

A ligand useful to form a metallocene olefin polymerization catalyst comprises:

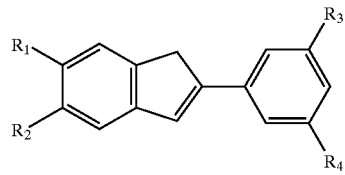

wherein at least $R_3$ and $R_4$ are substituents having at least a bulk of a t-butyl group and, optionally, wherein $R_1$ or $R_2$ may be a bulky substituent group.

26 Claims, No Drawings

OTHER PUBLICATIONS

Yokota et al., "Determination of Coisotacticities of Some Alternating Styrene–Acrylic Copolymers by NMR Spectra." J. of Poly Sci., 14, pp. 57–71 (1976).

Younkin et al., "Neutral, Single–Component Nickel (II) Polyolefin Catalysts That Tolerate Heteroatoms," Science, 287. pp. 460–462 (2000).

Collins et al., "Group Transfer Polymerization Cationic Zirconocene Compounds," J.Am.Chem.Soc., 1992, 114, pp. 5460–5462.

Giardello et al., "Stereocontrol in the Polymerization of Methyl Methacrylate Mediated by Chiral Organolanthanide Metallocenes," J.Am.Chem.Soc., 1995, 117, pp. 3276–3277.

Katritzky et al., "Carbon–13 Nuclear Magnetic Resonance Spectroscopy of Polymers. Part III. Determination of Tacticity in Monomer Sequence Distribution Triads in Styrene–Methyl Methacrylate Copolymer," J.Chem.Soc. Perkin Trans. 2, 1974, pp. 1547–1554.

Bataille et al., Study of the Parameters Controlling the Alternating Copolymerization of Methyl Methacrylate and Styrene, Chem.Eng. Comm., 1987, pp. 167–178.

Yasuda et al., "Synthesis of Monodispersed High Molecular Weight Polymers and Isolation of an Organolanthanide (III) Intermediate Coordinated by a Penultimate Poly(MMA) Unit," J. Am. ChemSoc., 1992, 114, pp. 4908–4910.

* cited by examiner

FLUXIONAL CATALYSTS AND RELATED LIGANDS CONTAINING BULKY SUBSTITUENTS

CROSS-REFERENCE TO RELATED APPLICATIONS

This application claims benefit of U.S. Provisional Application No. 60/112,383, filed Dec. 14, 1998, incorporated by reference herein.

STATEMENT REGARDING FEDERALLY SPONSORED RESEARCH OR DEVELOPMENT

This invention, in part, was made with Government support under ATP grant 70NANB5H1140 awarded by the National Institute of Standards and Technology. The United States Government may have certain rights in this invention.

BACKGROUND OF THE INVENTION

This invention relates to advantageous ligand systems and fluxional metallocene catalyst components made therefrom which are useful in producing olefin polymers and especially elastomeric propylene polymers.

Recently, a new class of metallocene-based catalyst systems has been described based upon unbridged substituted indenyl structures which have been identified as "fluxional." These systems are described in the Waymouth et al. U.S. Pat. No. 5,594,080, incorporated by reference herein. Fluxional metallocene components are based on aryl 2-substituted indenyl ligands that ore formed into a metallocene which incorporates a transition metal, including Group 4 (IUPAC Periodic System) metals such as titanium, zirconium, and hafnium. These fluxional catalysts in combination with an anionic co-catalyst such as methylaluminoxane or a borate or borane compound, may be used to produce olefin polymers including elastomeric propylene polymers.

U.S. Pat. No. 5,594,080 describes a series of fluxional catalyst systems which include catalysts prepared from 2-phenylindenyl ligands which form elastomeric propylene polymers. A theory set forth for these Waymouth catalyst systems is that the 2-aryl substituted indenyl ligands rotate about the central metal to form catalysts with differing symmetry. Characteristics of polymerized olefins will depend upon the rotational symmetry state of the catalyst. For example, propylene Will polymerize into isotactic segments when the catalyst is in a "rac" rotational symmetry state, while atactic segments will be formed while the catalyst is in a "meso" rotational symmetry state. Certain Waymouth-type metallocene structures are described in Published PCT Application WO 98/57996, incorporated by reference herein, which has common inventors to this application.

As reported by Waymouth et al., elastomeric polypropylene may be formed by fluxional catalyst systems. However, polymerization activities of the catalyst systems reported by Waymouth et al. remain modest and more active catalysts are needed for commercially-acceptable processes. Further, desirable properties for elastomeric polypropylene include reasonably high molecular weights as indicated by a low melt flow rate (MFR) and suitably high polymer crystallinities which are dependent on isotacticity measured by $^{13}C$ NMR, e.g. isotactic pentad content (% m4).

Fluxional catalyst systems have produced a variety "blocky" olefin polymers with advantageous polymer characteristics. A blocky polymer will contain segments of differing compositional microstructures. An example of a blocky polymer is a propylene polymer containing blocks of atactic and isotactic regions which may show plastomeric or elastomeric properties. Other examples of blocky polymers may contain co-monomers within the segments. The broad class of fluxional catalysts and polymers related to this invention are described in Waymouth et al. U.S. Pat. No. 5,594,080. However, in order to make production of polymers made from fluxional catalysts commercially practicable, catalysts with higher polymerization activities coupled with production of suitable polymers are needed. The catalysts described in this invention generally are more active compared to catalysts made with structurally similar ligands under comparable conditions.

SUMMARY OF THE INVENTION

A ligand useful to form a metallocene olefin polymerization catalyst comprises:

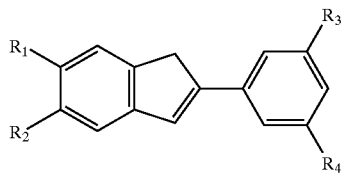

wherein at least $R_3$ and $R_4$ are substituents having at least a bulk of a t-butyl group and, optionally, wherein $R_1$ or $R_2$ may be a bulky substituent group.

BRIEF DESCRIPTION OF THE INVENTION

The present invention is an advantageous metallocene catalyst system based on a ligand system containing bulky substituents at least at the 3 and 5 phenyl positions as shown below:

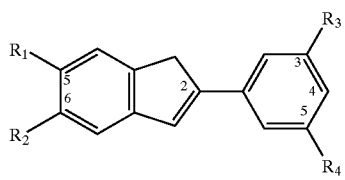

These bulky substituents are based on tertiary carbon or silicon. Typically these tertiary atoms are substituted with $C_1$–$C_4$ alkyl or substituted (with such as a halide) alkyl. The preferable bulky substituents are t-butyl and trimethylsilyl (TMS). A bulky substituent according to this invention has a spatial bulk (as indicated by steric or van der Waals repulsions) at least as large as a tertiary butyl group.

Optionally, bulky substituents may be placed at the 5 and 6 indenyl positions as shown above. Thus, the ligand systems of this invention contain at least one bulky substituent for groups $R_3$ and $R_4$, and optionally for $R_1$ and $R_2$.

Also, $R_1$ and $R_2$ may be connected to form a cycloaliphatic ring system containing 4 to 20 carbon atoms containing tertiary alpha carbon atoms as exemplified by 2-(3,5-di-t-butylphenyl)-5,5,8,8 tetramethyl-5,6,7,8-tetrahydrobenz(f)indene as shown below:

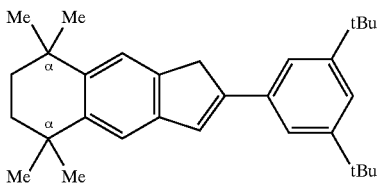

In more preferable ligands, both $R_3$ and $R_4$ are bulky and comprise t-butyl or trimethylsilyl (TMS).

Specific examples of ligands include $R_3$ and $R_4$ are t-butyl or TMS; $R_1$ and $R_2$ are t-butyl or TMS and $R_3$ and $R_4$ are t-butyl or TMS; $R_3$ and $R_4$ are t-butyl or TMS and $R_1$ and $R_2$ are connected to form a cyclohexyl with quaternary alpha carbon atoms; $R_1$ is t-butyl or TMS and $R_3$ and $R_4$ are t-butyl or TMS; and $R_1$ and $R_2$ are t-butyl or TMS and $R_3$ is t-butyl or TMS.

Bis metallocene catalyst components of this invention, especially bis hafnium and zirconium metallocene components, generally show higher olefin polymerization activity than metallocene components formed from structurally similar ligands. Further, polymerizations showing this increased activity typically produce polyolefins with sufficiently low melt flow rates (MFR as measured by ASTM D1238, Condition L) such that hydrogen or other agent may be used to control molecular weight to a useful melt flow range without the polymer transforming into an unsuitable low molecular weight product. Typically polymers formed from the catalysts of this invention without hydrogen have MFR's from below 1 to about 2. Addition of a molecular weight control agent may increase these polymers to a melt flow rate typically from about 1 up to about 100, typically about 1 to 35, and preferably about 2 to about 25. Further, propylene polymer crystallinities are dependent on isotacticity, a measure of which is percent of pentad and longer isotactic runs, measured by percent m4 (% m4), as determined by $^{13}C$ nmr techniques. Therefore, isotacticity (m4) is generally indicative of polymer properties. The relationship between polymer properties, crystallinity and isotacticity depends on the polymer structure (blockiness) and propagation statistics. Based on typical materials of this invention, an m4 content less than about 20% typically is an amorphorus gum elastomer which will draw to high elongation, but is very soft and inelastic and exhibits poor recovery and little or no tensile hardening at high strain (>500%) unless the molecular weight is extremely high. A polymer with an m4 content of about 20–25% to 40–45% typically is elastomeric and will exhibit recovery (>80%), hardening at high strain no yielding, and uniform specimen deformation. A polymer with an m4% of about 20 to 25% is borderline between amorphous and elastomeric. A polymer with an m4 content of about 40–45% to about 50–55% typically is plastomeric and will exhibit low to medium recovery (70–80%), strain hardening, low to no yielding, and some non-uniformity of specimen deformation. A polymer with an m4% of about 40 to 45% is borderline between elastomeric and plastomeric. A polymer with an m4 content of about 55 to 80+% typically is a soft polypropylene which is plastic which yields and draws. A polymer with an m4% of about 90 to 100% usually is described as isotactic polypropylene. For propylene polymers made from catalysts of this invention, products in the elastomeric and plastomeric range are preferred; elastomeric properties may be most preferred if elastomeric characteristics are desired.

Metallocene catalyst components may be formed by known techniques. Zirconium and hafnium metallocenes are preferred and hafnium metallocenes are most preferred. The Examples disclose methods for preparing the metallocenes in high yield. Generally, metallocenes are prepared by forming the indenyl ligand followed by metallation with the metal tetrahalide to form the complex in synthetic procedures known to the art.

Appropriate cocatalysts include alkylaluminum compounds, methylaluminoxane, or modified methylaluminoxanes, as illustrated in U.S. Pat. No. 4,542,199 to Kaminsky, et al.; Ewen, J. Am. Chem. Soc., 106 (1984), p. 6355; Ewen, et al., J. Am. Chem. Soc. 109 (1987) p. 6544; Ewen, et al., J. Am. Chem. Soc. 110 (1988), p. 6255; Kaminsky, et al, Angew. Chem., Int. Ed. Eng. 24 (1985), p. 507. Other useful cocatalysts include Lewis or protic acids, such as $B(C_6F_5)_3$ or $(PhNMe_2H)^+B(C_6F_5)_4^+$, which generate cationic metallocenes with compatible non-coordinating anions in the presence or absence of alkylaluminum compounds. Catalyst systems employing a cationic Group 4 (IUPAC Periodic Series) metallocene and compatible non-coordinating anions are described in U.S. Pat. Nos. 5,198,119, 5,198,401, and 5,223,467; Marks, et al., J. Am. Chem. Soc., 113 (1991), p. 3623; Chien, et al., J. Am. Chem. Soc., 113 (1991), p. 8570; Bochmann et al., Angew. Chem. Intl., Ed. Engl. 7 (1990), p. 780; and Teuben et al., Organometallics, 11 (1992), p. 362, and references therein; all incorporated by reference herein.

In one of many embodiments, these catalyst systems may be placed on a suitable support such as silica, alumina, or other metal oxides, magnesium halide such as $MgCl_2$ or other supports. These catalysts can be used in the solution phase, in slurry phase, in the gas phase, or in bulk monomer. Both batch and continuous polymerizations can be carried out. Appropriate solvents for solution polymerization include liquefied monomer, and aliphatic or aromatic solvents such as toluene, benzene, hexane, heptane, diethyl ether, as well as halogenated aliphatic or aromatic solvents such as methylene chloride, chlorobenzene fluorobenzone, hexaflourobenzene or other suitable solvents. Use of liquid hydrocarbon is preferred such as hexane or heptane is preferred to avoid halogenated waste streams. Various agents can be added to control the molecular weight, including hydrogen, silanes and metal alkyls such as diethylzinc.

Polymers made according to this invention are prepared by contacting one or more olefin monomers such as ethylene, propylene, or other $C_4$–$C_8$ alpha-olefin, with the above-described catalyst system under suitable polymerization conditions. Such conditions include polymerization or copolymerization temperature and time, pressure(s) of the monomer(s), avoidance of contamination of catalyst, choice of polymerization or copolymerization medium in slurry processes, the use of additives to control homopolymer or copolymer molecular weights, and other conditions well known to persons skilled in the art. Production of propylene and ethylene polymers is preferred.

Typically, sufficient amounts of catalyst or catalyst component is used for the reactor system and process conditions selected. The amount of catalyst will depend upon the activity of the specific catalyst chosen.

Irrespective of the polymerization or copolymerization process employed, polymerization or copolymerization should be carried out at temperatures sufficiently high to ensure reasonable polymerization or copolymerization rates and avoid unduly long reactor residence times, but not so high as to cause catalyst deactivation or polymer degradation. Generally, temperatures range from about 0° to about 120° C. with a range of from about 20° C. to about 95° C.

being preferred from the standpoint of attaining good catalyst performance and high production rates. A preferable polymerization range according to this invention is about 50° C. to about 80° C.

Olefin polymerization or copolymerization according to this invention is carried out at monomer pressures of about atmospheric or above. Generally, monomer pressures range from about 20 to about 600 psi (140 to 4100 kPa), although in vapor phase polymerizations or copolymerizations, monomer pressures should not be below the vapor pressure at the polymerization or copolymerization temperature of the alpha-olefin to be polymerized or copolymerized.

The polymerization or copolymerization time will generally range from about ½ to several hours in batch processes with corresponding average residence times in continuous processes. Polymerization or copolymerization times ranging from about 1 to about 4 hours are typical in autoclave-type reactions. In slurry processes, the polymerization or copolymerization time can be regulated as desired. Polymerization or copolymerization times ranging from about ½ to several hours are generally sufficient in continuous slurry processes.

Examples of gas-phase polymerization or copolymerization processes in which the catalyst or catalyst component of this invention is useful include both stirred bed reactors and fluidized bed reactor systems and are described in U.S. Pat. Nos. 3,957,448; 3,965,083; 3,971,786; 3,970,611; 4,129,701; 4,101,289; 3,652,527; and 4,003,712, all incorporated by reference herein. Typical gas-phase olefin polymerization or copolymerization reactor systems comprise at least one reactor vessel to which olefin monomer and catalyst components can be added and which contain an agitated bed of forming polymer particles. Typically, catalyst components are added together or separately through one or more valve-controlled ports in the single or first reactor vessel. Olefin monomer, typically, is provided to the reactor through a recycle gas system in which unreacted monomer removed as off-gas and fresh feed monomer are mixed and injected into the reactor vessel. A quench liquid, which can be liquid monomer, can be added to polymerizing or copolymerizing olefin through the recycle gas system in order to control temperature.

Irrespective of polymerization or copolymerization technique, polymerization or copolymerization is carried out under conditions that exclude oxygen, water, and other materials that act as catalyst poisons. Also, according to this invention, polymerization or copolymerization can be carried out in the presence of additives to control polymer or copolymer molecular weights. Hydrogen typically is employed for this purpose in a manner well known to persons of skill in the art. Although not usually required, upon completion of polymerization or copolymerization, or when it is desired to moderate or terminate polymerization or copolymerization or at least temporarily deactivate the catalyst or catalyst component of this invention, the catalyst can be contacted with water, alcohols, carbon dioxide, oxygen, acetone, or other suitable catalyst deactivators in a manner known to persons of skill in the art.

The polymerization of olefins according to this invention is carried out by contacting the olefin(s) with the catalyst systems comprising the transition metal fluxional component and in the presence of an appropriate cocatalyst, such as an aluminoxane, a Lewis acid such as $B(C_6F_5)_3$, or a protic acid in the presence of a non-coordinating counterion such as $B(C_6F_5)_4^-$.

Polymer produced according to this invention may be formed into pellets by melt extrusion and chopping, which then may be used to form useful articles such as fibers, films, and other fabricated products. Polymers of this invention may be combined with effective amounts of typical polymer additives known to the art such as heat and uv stabilizers, anti-oxidants, acid scavengers, anti-stat agents, and the like.

Our invention is illustrated, but not limited by, the following examples:

EXAMPLES 1–27 and

Comparative Runs C1–C16

Ligand Preparations

A series of ligands were prepared in order to prepare metallocene catalysts useful to illustrate our invention.

2-Phenylindene (Ligand A)

2-Phenylindene was prepared by the method described in Coates, G. W.; Waymouth, R. M. *Science* 267, 217 (1995).

2-(3,5-bis Trifluoromethylphenyl)indene (Ligand B)

2-(3,5-bis Trifluoromethylphenyl)indene was prepared by the method described in WO 98/57996.

3,4-Dimethylcinnamic Acid

A 1 L single-neck round bottom flask equipped with a condenser, magnetic stir bar, and a nitrogen inlet was charged with 3,4-dimethylbenzaldehyde (Lancaster 97%, 70.0 g, 0.52 mol), sodium acetate (anhydrous, 47.1 g, 0.57 mol), and acetic anhydride (300 mL, 3.2 mol). The mixture was stirred and heated to reflux. After 48 hours heating was discontinued and the reaction mixture was quenched, while still hot, by the cautious addition of water (300 mL). Ice-water was added to double the volume and the mixture was extracted with diethyl ether (700 mL); the organic phase was separated, washed with water (4×1 L), dried over anhydrous magnesium sulfate, and evaporated to dryness. Recrystallization of the crude product from methanol gave trans-3,4-dimethylcinnamic acid (64.0 g, 97% purity by GC) as yellow crystals. $^1$HNMR (CD$_2$Cl$_2$, 500 MHz) δ7.74 (d, JAB=16 Hz, 1H); 7.36 (br s, 1H); 7.32 (d, JAB=8 Hz, 1H); 7.18 (d, JAB=8 Hz, 1H); 6.41 (d, JAB=16 Hz, 1H); 2.29 (s, 6H).

3-(3,4-Dimethylphenyl)propionic Acid

A titanium 3 L stirred autoclave was charged with a solution of trans-3,4-dimethylcinnamic acid (64.0 g, 0.363 mol) in tetrahydrofuran (500 mL), ethanol (1 L), and 5% palladium on carbon (15 g, 50 wt % water). The reactor was sealed, purged with nitrogen, pressurized to 80 psi (550 kPa) with hydrogen and stirred at room temperature for 4 hours. The reaction mixture was transferred from the reactor, filtered, and evaporated to dryness to give 3-(3,4-dimethyl) propionic acid (64.1 g, 97+% purity by GC). $^1$HNMR (CD$_2$Cl$_2$) δ7.04 (d, JAB=7.5 Hz, 1H); 6.98 (s, 1H); 6.92 (d, JAB=7.5 Hz, 1H); 2.87 (t, J=8 Hz, 2H); 2.64 (t, J=8 Hz, 2H); 2.23 (s, 3H); 2.22 (s, 3H).

3-(3,4-Dimethylphenyl)propionyl Chloride

A 1 L three-neck round bottom flask equipped with a condenser, magnetic stir bar, thermometer, and a nitrogen inlet was charged with 3-(3,4-dimethylphenyl) propionic acid (64.0 g, 0.359 mol), dichloromethane (500 mL), and thionyl chloride (110 mL, 1.5 mol). The reaction mixture was stirred at reflux for 7 hours. Dichloromethane and excess thionyl chloride were removed by rotary evaporation under reduced pressure to yield 3-(3,4-dimethylphenyl) propionyl chloride as an amber oil (70.6 g, 100% conversion by GC).

5,6-Dimethyl-1-indanone

A 2 L three-neck round bottom flask equipped with a condenser, magnetic stir bar, thermometer, and a nitrogen inlet was charged with 3-(3,4-dimethylphenyl) propionyl chloride (70.6 g, 0.359 mol) and dichloromethane (anhydrous, 1.5 L). The solution was cooled to 15° C. and aluminum chloride (48.0 g, 0.36 mol) was added incrementally over 20 minutes. A temperature of 20° C. was maintained for 2 hours, then the dark red reaction mixture was quenched into 5% HCl (ice-water, 1.5 L). The organic phase was washed with water, then reduced to near dryness by rotary evaporation. The crude product was dissolved in diethyl ether (500 mL), washed with water, dried over anhydrous magnesium sulfate, and evaporated to dryness to yield a brown oil composed of 5,6-dimethyl-1-indanone and 6,7-dimethyl-1-indanone (60:40 mixture). Fractional crystallization in hexanes afforded the predominate, and less soluble, 5,6-dimethyl-1-indanone (21.65 g, 98+% purity by GC) as tan crystals. $^1$HNMR ($CD_2Cl_2$, 500 MHz) $\delta$7.46 (s, 1H); 7.27 (s, 1H); 3.04 (t, JAB=6 Hz, 2H); 2.60 (t, JAB=6 Hz, 2H); 2.34 (s, 3H); 2.30 (s, 3H).

5,6-Dimethyl-1-indanol

A 1 L three-neck round bottom flask equipped with a condenser, mechanical stirrer, nitrogen inlet and a thermometer was charged with 5,6-dimethyl-1-indanone (21.65 g, 0.133 mol) and ethanol (450 mL). The mixture was heated with stirring to 45° C. and sodium borohydride (15.2 g, 0.40 mol) was added incrementally over 10 minutes. The reaction mixture was then heated at reflux for 18 hours, cooled, quenched in 5% HCl (1 L ice-water), and extracted with diethyl ether (500 mL). The organic phase was separated, washed with water (3×500 mL), dried over anhydrous magnesium sulfate, and evaporated to dryness under reduced pressure to yield 5,6-dimethyl-1-indanol (23.0 g) as an amber oil. $^1$HNMR ($CD_2Cl_2$, 500 MHz) $\delta$7.12 (s, 1H); 7.01 (s, 1H); 4.81 (m, 1H); 2.95 (m, 1H); 2.72 (m, 1H); 2.28 (m, 1H); 2,26 (s, 3H); 2.23 (s, 3H).

5,6-Dimethylindene

A 1 L three-neck round bottom flask equipped with a condenser, mechanical stirrer, nitrogen inlet and a thermometer was charged with 5,6-dimethyl-1-indanol (41.25 g, 0.254 mol), toluene (250 mL), pyridine (250 mL, 3.1 mol), and p-toluenesulfonyl chloride (52.0 g, 0.273 mol). The mixture was heated to reflux and dehydration was monitored by GC. After 2.5 hours at reflux the reaction mixture was cooled, quenched in 5% HCl (1.2 L ice-water), and extracted with diethyl ether (500 mL). The organic phase was washed with 5% aqueous sodium bicarbonate, water, and then dried over anhydrous magnesium sulfate. Rotary evaporation followed by vacuum distillation (79° C./0.5 mm Hg) yielded 5,6-dimethylindene (30.1 g, 98+% purity by GC) as white crystalline solid (mp 34–35° C.). $^1$HNMR ($CD_2Cl_2$, 500 MHz) $\delta$7.24 (s, 1H); 7.16 (s, 1H); 6.80 (m, 1H); 6.45 (m, 1H); 3.32 (s, 2H); 2.28 (s, 6H).

2-Bromo-5,6-dimethylindene

A 300 mL three-neck round bottom flask equipped with a condenser, mechanical stirrer, thermometer, and an addition funnel was charged with 5,6-dimethylindene (8.0 g, 56 mmol), tetrabutylammonium chloride (0.25 g), and water (100 mL). The addition funnel was charged with a solution of bromine (9.4 g, 0.059 mol) and potassium bromide (7.0 g, 0.059 mol) in water (100 mL total volume). The aqueous emulsion of 5,6-dimethylindene was vigorously stirred, at 45° C., during the course of a 30 minute dropwise addition of the bromine-bromide solution. Stirring was continued for another 2.5 hours at 50° C. The almost colorless reaction mixture was then cooled, diluted with water (100 mL), and diethyl ether (200 mL). The organic phase was separated, washed with water (3×200 mL), dried over anhydrous magnesium sulfate, and evaporated to near dryness. GC-MS analysis of the crude product revealed a 96% conversion of 5,6-dimethylindene. The expected 2-bromo-5,6-dimethyl-1-indanol comprised the majority of the mixture followed, in order of abundance, by 2-bromo-5,6-dimethylindene (via dehydration of the indanol), 1,2-dibromo-5,6-dimethylindane, and unreacted 5,6-dimethylindene. The entire quantity of crude product was transferred to a 300 mL three-neck round bottom flask equipped with a condenser, magnetic stir bar, and a nitrogen inlet. Toluene (200 mL), and p-toluenesulfonic acid (0.05 g) were added and the mixture was heated to reflux. GC analysis showed that the dehydration of 2-bromo-5,6-dimethyl-1-indanol was complete after 3 hours at reflux. The reaction mixture was cooled and extracted with diethyl ether (100 mL). The organic phase was separated, water washed, dried over anhydrous magnesium sulfate, and evaporated to yield crude 2-bromo-5,6-dimethylindene (11.2 g) as white oily crystals. One recrystallization from ethanol followed by two consecutive recrystallizations from hexanes gave purified 2-bromo-5,6-dimethylindene (6.5 g. 94% purity by GC) as white crystals.

2-(4-Methylphenyl)-5,6-dimethylindene (Ligand C)

A dry 100 mL three-neck round bottom flask equipped with a condenser, magnetic stir bar, thermometer, and a nitrogen inlet was charged with 2-bromo-5,6-dimethylindene (6.0 g, 0.027 mol), anhydrous diethyl ether (35 mL), p-tolylmagnesium bromide (26.9 mL of 1 M in diethyl ether, 0.027 mol), and [1,2-bis(diphenylphosphino)ethane]nickel(II)chloride (0.2 g, 0.38 mmol). The reaction mixture reached a gentle reflux without heating. After the exotherm subsided the mixture was heated. Precipitation of magnesium bromide was observed during the course of the reaction and after 6 hours at reflux the resulting mixture was cooled, quenched into chilled aqueous HCl (1 M, 200 mL), and extracted with diethyl ether (100 mL).

The organic phase was separated, water washed, and dried over anhydrous magnesium sulfate. Slow evaporation of the diethyl ether allowed for selective crystallization of the major by-product, 4,4'-dimethylbiphenyl, which then was separated by filtration. The filtrate was evaporated to dryness and the residue recrystallized three consecutive times from methanol-acetone to yield 2(4-methylphenyl)-5,6-dimethylindene (4.1 g, 99+% purity by GC) as white crystals (mp 227–8° C.). $^{HNMR}$ ($^{CD}_2Cl_2$, 500 MHz) $\delta$7.52 (s, 1H); 7.52 (s, 1H); 7.24 (s, 1H); 7.19 (s, 1H); 7.17 (s, 1H); 7.15 (s, 1H); 7.12 (s, 1H); 3.70 (s, 2H); 2.35 (s, 3H); 2.29 (s, 3H); 2.28 (s, 3H).

Bromo-3,5-di-t-butylbenzene 1,3,5-Tri-t-butylbenzene (150 g, 0.6 mol) was dissolved in carbon tetrachloride (300 mL) in a three-necked flask which had been painted black to avoid light and equipped with an overhead stirrer, thermometer and addition funnel under argon. Iron pellets (36 g. 0.64 mol) were added and the slurry was cooled to 5° C. t-Butylcatechol (1.0 g) was added and a solution of bromine (201.6 g, 1.26 mol) in carbon tetrachloride (75 mL) was added over a one hour period. The slurry was stirred for an additional 4 hours at 5° C. and quenched by pouring into ice water. The layers were separated and the organics washed with 10% sodium hydroxide solution. The solution then was washed with salt brine and dried over magnesium sulfate. The solvent was evaporated and the product was distilled under vacuum twice to give 75 g of product which was then recrystallized from heptane to give 47 g of pure product (29% yield).

2-(3,5-Di-t-butylphenyl)indene (Ligand D)

1-Bromo-3.5-di-t-butylbenzene (47.2 g, 0.175 mol) was dissolved in ether (500 mL) and cooled to −70° C. t-Butyllithium (200 mL of 1.7 M solution in pentane, 0.34 mol) was added at −70° C. over a two-hour period. The solution was allowed to warm to room temperature slowly. Magnesium bromide etherate (46.5 g. 0.18 mol) was added and the slurry was stirred for one hour. The mixture was then cooled to 5° C. and 2-bromoindene (34.2 g, 0.18 mol) was added. The mixture was warmed to room temperature and then refluxed for three hours. The solution was cooled to room temperature and the reaction was quenched carefully with water. The layers were separated and the organics washed with salt brine and dried over magnesium sulfate. The solvents were evaporated and the product was distilled twice and recrystallized from hexane to give 37.1 g of product (70% yield).

3,5 Bis(trimethylsilyl)bromobenzene 1,3,5-Tribromobenzene (125 g, 0.4 mol) was dissolved in anhydrous diethylether (1 L), and cooled to −70° C. n-butyllithium (250 mL. 1.6 M in hexanes. 0.4 mol) was added dropwise over a one-hour period keeping the temperature near −70° C. The solution was stirred for an additional 20 minutes at −70° C. and then warmed to −10° C. over a two-hour period. The solution was then recooled to −70° C. and trimethylchlorosilane (45 g, 0.4 mol) was added over a one-hour period. The solution was stirred and allowed to warm to room temperature overnight. The solution was cooled to −70° C. and an additional 0.4 mol n-butyllithium was added over a one-hour period. The resulting slurry was stirred for one hour at −70° C., warmed to −10° C. over a one-hour period and then recooled to −70° C. An additional 0.4 mol of trimethylchlorosilane was added and the slurry was allowed to warm to room temperature overnight. The mixture was quenched with water and the layers were separated. The organic layer was washed twice with sodium bicarbonate solution and with salt brine then dried over magnesium sulfate. The solvents were evaporated under vacuum and the product distilled twice under vacuum to yield 85.2 g (70%) of a colorless liquid. b.p. 100–105° C. at 0.5 mmHg.

2-(3,5-Bis(trimethylsilyl))indene (Ligand E)

Magnesium turnings (6.8 g, 0.28 mol) and anhydrous THF (100 mL) were placed in a three-necked flack under argon. A solution of 3,5-bis(trimethylsilyl)bromobenzene (85.2 g, 0.28 mol) in THF (100 mL) was added incrementally to the THF and magnesium mixture while keeping the temperature near reflux. The Grignard reaction started immediately after the addition of the first increment. The remaining solution was added over a one-hour period. The resulting slurry was refluxed for an additional 30 minutes. The solution was cooled to 20° C. and a solution of 2-indanone (36.7 g. 0.28 mol) in ether (100 mL) was added dropwise over a one-hour period. The solution then was stirred at room temperature overnight. The solution was neutralized with 1 N HCl. The aqueous layer was separated and washed three times with 100 mL of ether. The organics were combined and dried over magnesium sulfate. The solvents were evaporated to yield a tan solid of the crude alcohol. This solid was taken up in acetic acid (200 mL) and cooled to 15° C. A solution of sulfuric acid (40 g) and of acetic acid (200 mL) was added slowly, keeping the temperature of the mixture near 15° C. The product separated as an oil. The acetic acid layer was diluted with 1 L of ice water and extracted with toluene. The organic layer was separated and washed twice with sodium bicarbonate solution and dried over magnesium sulfate. The solvents were evaporated. The product then was taken up in a minimal amount of hexanes and passed through a short silica gel column to remove very polar material. Attempts to crystallize the product failed and the product was distilled to yield 20.5 g (22% yield), b.p. 175–180° C. at 0.3 mm Hg. This procedure was repeated to yield an additional 22.3 grams of material. $^1$H NMR ($C_6D_6$); $\delta$7.45 (2H,s), 7.26(1H,s), 7.13(2H,d), 6.94 (1H,m), 6.85 (2H,m), 3.51(2H,s).

4-t-Butylcinnamic Acid

A 3 L one neck flask fit with a reflux condenser, magnetic stirrer, and nitrogen inlet was charged with p-t-butylbenzaldehyde (145.5 g, 0.90 mol), acetic anhydride (106 mL, 1.12 mol), and sodium acetate (7.36 g, 0.90 mol). After refluxing for 48.5 hours the reaction was cooled and water was added slowly to roughly triple the total volume as a yellow solid formed. The solids were filtered and washed with water (200 mL), reslurried in water and refiltered and washed again with water (750 mL total). The product was partially dried in the vacuum oven to give 4-t-butlycinnamic acid (248 g). $^1$HNMR ($CD_3SOCD_3$, 500 MHz) mostly trans isomer $\delta$7.58 (d, JAB=8.5 Hz, 2H); 7.54 (d, J=15.5 Hz, 1H); 7.41 (d, JAB=7.5 Hz, 2H); 6.46 (d, J=16.0 Hz, 1H); 1.26 (s, 9H).

3-(4-t-Butylphenyl)propionic Acid

A 3 L autoclave was charged with wet t-butylcinnamic acid (248 g, 1.21 mol), tetrahydrofuran (1 L), and ethanol (1 L) and palladium on carbon (35 g). The reactor was shut and 90 psi of hydrogen pressure applied and the reactor held at room temperature overnight. The reaction was then transferred to a round bottom flask and concentrated to 200 mL. The formed crystals were decanted and washed with hexane to give 3-(4-t-butylphenyl)propionic acid (52.9 g after vacuum drying). A second crop from the filtrate yielded additional 3-(4-t-butylphenyl)propionic acid (65.8 g). $^1$HNMR ($CD_2Cl_2$, 500 MHz) $\delta$9.85 (br s, 1H); 7.32 (d, J=8 Hz, 2H); 7.15 (d, JAB=8.5 Hz); 2.91 (t, J=8 Hz, 2H); 2.67 (t, J=8 Hz, 2H); 1.27 (s, 9H).

3-(4-t-Butylphenyl)propionyl Chloride

A 2 L 3 neck round bottom flask fit with a condenser, thermometer, nitrogen inlet, and overhead stirrer was charged with 3-(4-t-butylphenyl)propionic acid (118.7 g, 0.576 mol),thionyl chloride (210 mL, 2.88 mol), dimethylformamide (3 drops), and methylene chloride solvent. The reaction was refluxed for 3 hours and additional 3-(4-t-butylphenyl)propionic acid (8.17 g, 0.040 mol) was added to the reactor and refluxed for an additional hour. After allowing to stand overnight, the reaction was stripped of volatiles to yield the crude 3-(4-t-butylphenyl)propionyl chloride (99.0 g). $^1$HNMR (CDCl$_3$, 500 MHz) δ7.33 (d, JAB=8 Hz, 2H); 7.12 (d, JAB=8 Hz, 2H); 3.20 (t, J=7.5 Hz, 2H); 2.98 (t, J=7.5, 2H); 1.31 (s, 9H).

6-t-Butyl-1-indanone

A 3 neck round bottom flask fit with a thermometer, nitrogen inlet, condenser, overhead stirrer, and solids addition funnel was charged with 3-(4-t-butylphenyl)propionyl chloride (99.0 g, 0.442 mol) and methylene chloride (2.0 L). The reaction mixture was cooled to 10 C. and aluminum chloride (62.1 g, 0.466 mol) was added slowly to the reaction mixture. After allowing the reaction to warm to room temperature and stir overnight the reaction was quenched into 5% HCl/ice (1 L). The organics were washed with water (10×200 mL), filtered through celite, and dried over anhydrous sodium sulfate. The solvents were removed by rotary evaporation to yield the crude 6-t-butyl-1-indanone (109 g). $^1$HNMR (CDCl$_3$, 500 MHz) δ7.79 (d, J=1.5 Hz, 1H); 7.66 (dd, JAB=2.8 Hz, 1H); 7.42 (d, J=8 Hz, 1H); 3.10 (t, J=6 Hz, 2H); 2.70 (t, J=6 Hz, 2H); 1.34 (s, 9H).

6-t-Butyl-1-indanol

A 3 L one neck flask fit with an overhead stirrer, condenser, nitrogen inlet, solids addition funnel, and thermometer was charged with crude 6-t-butyl-1-indanone (109 g, 0.577 mol) and anhydrous ethanol (1.5 L). The reaction was heated to 30–40° C. and sodium borohydride (43.6 g, 1.15 mol) was added over the course of 30 min followed by heating to reflux overnight. The next day an additional amount of sodium borohydride is added (12.0 g, 0.32 mol) and reflux continued for an hour. The reaction was cooled, quenched in 5% HCl/ice (1 L), extracted into diethyl ether (1 L), and the organic layer washed with water (14×150 mL), and dried over anhydrous sodium sulfate. Rotary evaporation to remove the solvent gave crude 6-t-butyl-1-indanol (64.4 g). Another diethyl ether extraction as above gave an additional amount of crude 6-t-butyl-1-indanol (75.5 g total). $^1$HNMR (CDCl$_3$, 500 MHz) δ7.46 (s, 1H); 7.32 (dd, JAB=1.5, 8 Hz, 1H); 7.19 (d, JAB=8 Hz, 1H); 5.24 (t, J=6 Hz); 3.01 (m, 1H); 2.78 (p, J=7.5 Hz, 1H); 2.50 (m, 1H); 1.95 (m, 1H); 1.32 (s, 9H).

6-t-Butylindene

A 2 L three neck flask fit with an overhead stirrer, condenser, nitrogen inlet, solids addition funnel, and thermometer was charged with 6-t-butyl+1-indanol (55.0 g, 0.29 mol), pyridine (117 mL, 1.45 mol), p-toluenesulfonyl chloride (60.7 g, 0.32 mol), and toluene (150 mL). The reaction was heated at 50° C. overnight, additional p-toluenesulfonyl chloride (27.5 g, 0.14 mol) added, and heated gradually to 70° C. for approximately 3 hours. The reaction was then cooled, quenched in concentrated HCl (75 mL)/ice (500 mL), extracted into diethyl ether (300 mL), the organics washed with sodium bicarbonate solution, water, and dried over anhydrous sodium sulfate. The crude was rotary evaporated after passing through alumina and distilled (25–90° C./0.3–0.5 mm Hg) to yield crude 6-t-butylindene (74.0 g) contaminated with p-toluenesulfonyl chloride. After washing with aqueous base and numerous recrystallizations from cold pentane, a crude sample of 6-t-butylindene (14.0 g) was obtained and used in the next step. $^1$HNMR (CDCl$_3$, 500 MHz) mixture of isomers—major isomer reported δ7.51 (d, J=1.5 Hz, 1H); 7.45 (d, JAB=8 Hz, 1H); 7.30 (dd, JAB=1.5 8 Hz, 1H); 6.92 (br d, J=5 Hz, 1H); 6.59 (m, 1H); 3.41 (s, 2H); 1.41 (s, 9H).

2-(3,5-Di-t-butylphenyl)-5-t-butylindene (Ligand F)

A 100 mL round bottom flask fit with an N$_2$ inlet, condenser, magnetic stirrer, and oil bath, was charged with crude 5-t-butyl indene (5.0 g, 0.930 mol), 3,5-di-t-butylbromobenzene (8.2 g, 0.030 mol), palladium(II) acetate (1.0 g, 0.0043 mol), tri-o-tolylphosphine (2.5 g, 0.0085 mol), triethylamine (3.4 g, 0.034 mol), and dimethylformamide (60 mL). The reaction mixture was then heated to 60° C. and allowed to stir for 72 hours. Afterwards GC analysis showed complete conversion of the starting material. The organics were dissolved in diethyl ether, washed with 1 M HCl (200 mL), 5% NaHCO$_3$ solution (200 mL), and 5% NaCl solution (200 mL), dried over MgSO$_4$, and stripped by rotary evaporation leaving crude material GC—50% pure by GC. The crude was purified by column chromatography oh silica/hexane to yield 7.9 g of product which was carefully tritrated repeatedly with methanol to yield 2-(3,5-di-t-butylphenyl)-5-t-butyl indene (3.72 g). $^1$HNMR (CDCl$_3$, 500 MHz) 50:50 mixture of alkene isomers; δ7.53 (s, 1H); 7.49 (br s, 4H); 7.45 (d, J=1 Hz, 1H); 7.40 (d, JAB=7.5 Hz, 1H); 7.37 (br s, 2H); 7.32 (s, 2H); 7.23 (br s, 2H); 7.20 (s, 2H); 3.81 (s, 2H); 3.79 (s, 2H); 1.37 (s, 18H).

5-Bromo-1-indanol

A 2 L three-neck round bottom flask equipped with a condenser, mechanical stirrer, nitrogen inlet and a thermometer was charged with 5-bromo-1-indanone (Aldrich 98%, 50.0 g, 0.24 mol) and ethanol (700 mL). The resulting suspension was warmed, with stirring, to 40° C. and sodium borohydride (18.2 g, 0.48 mol) was added incrementally over 20 minutes. A moderate exotherm ensued which brought the reaction to reflux. Heating was applied to maintain reflux for 14 hours. The reaction mixture was then cooled slightly, excess ethanol was removed by rotary evaporation, water (1 L) and diethyl ether (600 mL) were added. The organic phase was separated, washed several times with water (6×500 mL), and dried over anhydrous magnesium sulfate. Evaporation of the diethyl ether gave a quantitative yield of 5-bromo-1-indanol (50.5 g, 0.24 mol) crystals. $^1$HNMR (CD$_2$Cl$_2$, 500 MHz) δ7.39 (s, 1H); 7.35 (dd, JAB=1, 8 Hz, 1H); 7.26 (d, JAB=8 Hz, 1H); 5.17 (br s, 1H); 3.00 (m, 1H); 2.80 (p, J=8 Hz, 1H); 2.46 (m, 1H); 1.92 (m, 1H); 1.86 (s, 1H).

5-Bromoindene

A 1 L three-neck round bottom flask equipped with a condenser, magnetic stir bar, nitrogen inlet, and a thermometer was charged with 5-bromo-1-indanol (56.5 g, 0.265 mol), toluene (300 mL), pyridine (250 mL, 3.1 mol), and p-toluenesulfonyl chloride (55.3 g, 0.29 mol). The mixture was stirred and heated to reflux while dehydration progress was followed by GC. After 7 hours at reflux the dark colored reaction mixture was cooled, quenched by pouring over ice-water (700 mL) containing HCl (12M, 200 mL) and extracted several times with diethyl ether (3×250 mL). The combined diethyl ether extracts were washed repeatedly with water, 5% sodium bicarbonate (aqueous), and water then dried over anhydrous magnesium sulfate. Evaporation of diethyl ether followed by vacuum distillation (80° C./0.5 mm Hg) gave 5-bromoindene (24.0 g, 99+% purity by GC) as a colorless oil. $^1$HNMR (CD$_2$Cl$_2$, 500 MHz) δ7.59 (br s, 1H); 7.38 (dd, JAB=1.5, 8 Hz, 1H), 7.26 (d, JAB=8 Hz, 1H); 6.84 (m, 1H); 6.56 (m, 1H); 3.39 (s, 2H).

5-Phenylindene

A dry 100 mL three-neck round bottom flask equipped with a condenser, magnetic stir bar, thermometer, and a nitrogen inlet was charged with 5-bromoindene (99+% purity, 9.65 g, 50 mmol), diethyl ether (anhydrous, 60 mL), and phenylmagnesium bromide (18.0 mL 3M in diethyl ether, 54 mmol). The mixture was chilled to 10° C. and [1,2-bis(diphenylphosphino)ethane]nickel(II) chloride (0.1 g, 0.2 mmol) was added. The reaction mixture was warmed gradually to reflux. As the reaction progressed the clear solution became turbid from the precipitation of magnesium bromide by-product. After 4 hours at reflux the reaction mixture was quenched in chilled 5% aqueous HCl (200 mL). Additional diethyl ether (100 mL) was added and the organic phase was separated, water washed, and dried over anhydrous magnesium sulfate. Evaporation of diethyl ether followed by vacuum distillation (90° C./0.5 mm Hg) gave 5-phenylinene (8.4 g, 97% purity by GC) as pale yellow crystals. $^1$HNMR (CD$_2$Cl$_2$, 500 MHz) 50:50 mixture of isomers; δ7.72 (s, 1H); 7.62 (m, 5H); 7.52 (t, J=8 Hz, 2H); 7.43 (m, 6H); 7.32 (m, 2H); 6.93 (m, 2H); 6.61 (m, 2H); 3.47 (s, 2H); 3.44 (s, 2H).

2-(3,5-Di-tert-butylphenyl)-5-phenylindene

A 100 mL three-neck round bottom flask equipped with a condenser, magnetic stir bar, thermometer, and a nitrogen inlet was dried, purged with nitrogen, then charged with 5-phenylindene (5.8 g, 0.03 mol), 3,5-di-tert-butylbromobenzene (8.1 g, 0.03 mol), sodium acetate (4.9 g, 0.06 mol), dichloropalladium (II) bis(acetonitrile) (0.026 g, 0.10 mmol), tetraphenylphosphonium chloride (0.225 g, 0.60 mmol), and anhydrous 1-methyl-2-pyrrolidinone (45 mL). The reaction mixture was heated to 60° C. for 24 hours without any conversion of starting materials. The temperature was then raised to 140° C. for 16 hours after which GC analysis showed >95% conversion of 5-phenylindene. The reaction mixture was cooled, mixed with chilled 5% aqueous HCl (250 mL) and extracted with diethyl ether (3×100 mL). The combined diethyl ether extracts were water washed and then dried over anhydrous magnesium sulfate. Rotary evaporation gave crude product (12.5 g) as a viscous red-brown oil. Crystals of 2-(3,5-di-tert-butylphenyl)-5-phenylindene (6.4 g) precipitated from a concentrated solution (~50%) of the crude product in acetone-methanol (70:30). Three consecutive recrystallizations from acetone-methanol yielded 2-(3,5-di-tert-butylphenyl)-5-phenylindene (3.2 g, 99.9% purity by GC) as pale tan crystals (mp 122–3° C.). $^1$HNMR (CD$_2$Cl$_2$, 500MHz) 40:60 mixture of isomeric alkenes; δ7.65–7.25 (mults, 12H); 3.82, 3.80 (s, 2H); 1.30 (s, 18H).

3,5-Di-t-butylbenzoyl Chloride 3,5-Di-t-butylbenzoic acid, purchased from Aldrich Chemical Co., (10 g, 0.042 mol) was dissolved in 50 mL thionyl chloride and the light yellow solution was refluxed for 3 h under argon. The reaction was cooled to room temperature and excess SOCl$_2$ was evaporated under vacuum (liq. N$_2$ trap). The resulting oil was dissolved in dry toluene (100 mL) and the resulting solution was evaporated under vacuum to give the 3,5-di-t-butylbenzoyl chloride as a light brown oil (10.5 g, 99%).

4-(3,5-Di-t-butylphenyl)-hepta-1,6-diyne-4-ol

Magnesium turnings (4 g, 0.16 mol) and mercuric chloride (1.4 g, 6.12 mmol) were added under argon to a flame-dried three neck flask fitted with a condenser, an addition funnel, and a septum. Anhydrous diethyl ether (50 mL) was added to the flask via the cannula and the flask was cooled to 0° C. A solution of propargyl bromide (20 g, 0.17 mol) in dry diethyl ether (50 mL) was added dropwise via the addition funnel over a period of 1 h. The addition rate was maintained such that the temperature remained between 0° and 10° C. to avoid formation of propynyl Grignard. The Grignard reaction started almost immediately and the solvent turned greenish-gray during the addition. The reaction was stirred at 0° C. for 3 h. The propargyl Grignard solution was used immediately without isolating or allowing to warm above 0° C.

Using the propargyl Grignard solution (0.16 mol), anhydrous diethyl ether (50 mL) was added to the flask via cannula and the flask was cooled to −78° C. The acid chloride from the previous step (10.31 g, 0.04 mol) was dissolved in ether (25 mL) and added dropwise via an addition funnel. The color slowly changed from gray to yellow with white precipitate during the first fraction. Additional diethyl ether (30 mL) was added and the reaction was stirred for 1 h. The reaction was then warmed to room temperature and the mixture was quenched with 100 mL of ice water followed by the slow addition of 200 mL of cold 1 N HCl (causing vigorous bubbling), turning the organic layer deep red. The acidic aqueous layer was extracted with ether (3×200 mL), and the organic layers were collected and dried over MgSO$_4$. The red-orange solution was filtered and the ether was evaporated under vacuum to give the product as a red oil, which was purified by passing it through a silica column with hexanes to give 13.3 g of 4-(3,5-di-t-butylphenyl)-hepta-1,6-diyne-4-ol (95% yield).

2-(3,5-Di-t-butylphenyl)-2-hydroxyl-5-trimethylsilylindane

A solution of cyclopentadienylcobalt dicarbonyl (50 mL, 0.4 mmol) in bis(trimethylsilyl)acetylene (100 mL, excess) was placed in a flame-dried flask under argon. The flask was fitted with a reflux condenser and capped with a septum. The solution was heated to reflux under a slight pressure of argon. A solution of 4-(3,5-di-t-butylphenyl)heptane-1,6-diyne-4-ol (13.3 g, 0.039 mol) in bis(trimethylsilyl) acetylene (40 mL) was added to the refluxing solution with a syringe pump at a rate of approximately 0.5 mL/h. The reaction was allowed to reflux for 24 h after the addition was complete (total of 96 h). The reaction was cooled to room temperature and the bis(trimethylsilyl)acetylene was vacuum-transferred to another flask for use in future reactions. The residue, was identified by NMR as 2-(3,5-di-t-butylphenyl)-2-hydroxyl-5-trimethylsilylindane. This product was purified by passing through silica gel to give a yield of 10.2 g (80% yield).

2-(3,5-Di-t-butylphenyl)-5-trimethylsilylindene (Ligand G)

2-(3,5-Di-t-butylphenyl)-2-hydroxyl-5-trimethylsilylindane (10.2 2 g, 0.036 mol) was dissolved in 100 mL glacial acetic acid. Toluene (20 mL) was added to help dissolve the alcohol. The solution was cooled to 0° C. and a solution of concentrated sulfuric acid (10 g) in glacial acetic acid (30 mL) was added dropwise over a period of 40 min. The reaction was stirred at 0° C. for 20 min. The dark brown liquid was poured into a 4 L Erlenmeyer flask containing 500 g of ice and 500 mL of water. The mixture was separated into a yellow aqueous layer and a dark brown toluene layer. The aqueous layer was extracted with toluene (3×100 mL). The toluene layers were collected and washed with saturated NaHCO$_3$ solution (2×200 mL), then saturated NaCl solution (1×100 mL). The toluene was evaporated under reduced pressure to give a very dark oil. The oil was purified by flash chromatography on silica gel. Eluting with hexanes gave a fast moving yellow band, which was collected and recrystallized from hexanes to give 3.2 g, (33% yield) of product, identified by NMR as 2-(3,5-di-t-butylphenyl)-5-trimethylsilylindene. $^1$HNMR (CDCl$_3$, 500 MHz) δ7.58 (s, 1H); 7.51–7.47 (m, 3H); 7.38 (br s, 1H); 7.35 (d, JAB=7.5 Hz, 2H); 7.25 (s, 1H); 3.82 (s, 2H); 1.38 (s, 18H); 0.30 (s, 9H).

3,5-Di-t-butylbromobenzene 1,3,5-Tri-t-butylbenzene (150 g, 0.6 mol) was dissolved in 600 mL of carbon tetrachloride in a three-neck flask painted black to avoid light; The flask was equipped with an overhead stirrer, a thermometer, and an addition funnel under argon. Ferric chloride (3.0 g, 0.018 mol) was added and the solution was cooled to 0° C. A solution of bromine (120 g, 0.75 mol) dissolved in 200 mL of carbon tetrachloride was then added over a 2-hour period. The solution was stirred for an additional 1 hour at 0° C. and quenched with ice water. The layers were separated and the organics washed with 10% sodium hydroxide solution. The solution was then washed with salt brine and dried over magnesium sulfate. The solvent was removed under vacuum and the product was distilled through a 2-ft (60-cm) column under vacuum two times. The fractions boiling at 90°–110° C. at 0.4 mm Hg were combined and recrystallized from heptane to give 100 g of pure 3,5-di-t-butylbromobenzene (60% yield).

2-(3,5-Di-t-butylphenyl)-5,6-dimethylindene (Ligand H)

A 100 mL three-neck round bottom flask equipped with a condenser, magnetic stir bar, thermometer, and a nitrogen inlet was dried, purged with nitrogen, then charged with 5,6-dimethylindene (2.90 g, 20.1 mmol), 3,5-di-tert-butylbromobenzene (5.41 g, 20.1 mmol), anhydrous sodium acetate (3.28 g, 40.2 mmol), tetraphenylphosphonium chloride (0.45 g, 1.2 mmol), dichloropalladium (II) bis(acetonitrile) (0.05 g, 0.2 mmol), and anhydrous 1-methyl-2-pyrrolidinone (45 mL). The mixture was stirred and heated to 100° C. GC analysis showed 60% conversion of starting materials after 24 hours and complete conversion by 96 hours. The reaction mixture was cooled, poured into 1 M HCl (200 mL), and extracted with diethyl ether (200 mL). The organic phase was washed with water, dried over anhydrous magnesium sulfate, and rotary evaporated under reduced pressure to give an orange oil containing small suspended crystals. Dilution with hexanes (100 mL), chilling and stirring induced the precipitation of more crystals. The hexanes insoluble by-product 2-phenyl-5,6-dimethylindene (0.37 g) was removed by filtration. The hexanes filtrate was decolorized by passing it through a 50 cc column layered with silica gel and activated carbon (Darco G-60). Evaporation of the hexanes gave crystals which proved to be a mixture (3:1) of 2-(3,5-di-tert-butylphenyl)5,6-dimethylindene and its regioisomer 3-(3,5-di-tert-butylphenyl)-5,6-dimethylindene. Two successive recrystallizations of the mixture from concentrated chilled pentane solutions effectively separated the less soluble isomer and yielded[ u]pon evaporation of solvent, 2-(3,5-di-tert-butylphenyl)-5,6-dimethylindene (1.6 g, 90+% purity by GC). Subsequent recrystallization from methanol afforded pure 2-(3,5-di-tert-butylphenyl)-5,6-dimethylindene (1.35 g, 99.9+% purity by GC) as white crystals. $^1$HNMR (CD$_2$Cl$_2$, 500 MHz) δ7.47 (br s, 2H); 7.35 (s, 1H); 7.25 (s, 1H); 7.16 (br s, 2H); 3.75 (s, 2H); 2.30 (s, 3H); 2.29(s, 3H); 1.36 (s, 18H).

Benz[f]indene

α,α,α',α'-Tetrabromo-o-xylene (200 g, 0.48 mole) was dissolved in 2000 mL of dimethylformamide. 2-Cyclopentene-1-one (40 g, 0.25 mole) was added, along with 500 g sodium iodide. The mixture was heated overnight at 80° C. The mixture was cooled and poured into 2 L of ice water containing sodium bisulfide (20 g). The solids were collected and recrystallized from ethanol to give 65 g of benz[f]indan-1-one. The benzindanone was then reduced by dissolving in 600 mL of ethanol and adding 30 g of sodium borohydride, over a 2-hour period. The solution was stirred at room temperature overnight and quenched with 1 N HCl. The ethanol was removed under vacuum, and the product extracted into toluene. The product was then recrystallized from hexanes to give 58 g of benz[f]indan-1-ol. The benzindanol was then dehydrated by refluxing in 100 mL of 10% sulfuric acid overnight. The solution was cooled and extracted with toluene. The product was purified by column chromatography, in hexanes, followed by two recrystallizations from ethanol, and a final recrystallization from hexane to give 10.8 g (13% overall yield) of Benz[f]indene.

2-(3,5-Di-t-butylphenyl)benz[f]indene (Ligand J)

Benz[f]indene (10.8 g, 0.065 mole) was dissolved in 100 mL of dimethylformamide. 1-Bromo-3,5-di-t-butylbenzene (14 g, 0.052 mole) was added along with palladium acetate (0.3 g), tri-o-tolylphosphine (0.8 g), and triethyl amine (11.0 g). The solution was heated to 60° C. for 3 days. The solution was cooled and washed with 1 N HCl and by saturated sodium bicarbonate. The product was found to be difficult to separate from the residual tri-o-tolylphosphine. After purifying by passing through silica with hexanes three times, and recrystallization from ethanol, followed by three recrystallizations from hexanes, it yielded 5.8 g of 2-(3,5-di-t-butylphenyl)benz[f]indene (26% yield). $^1$HNMR (CDCl$_3$, 300 MHz δ7.95–7.77 (m, 4H); 7.52–7.37 (m, 5H); 7.23 (s, 1H); 3.99 (s, 2H); 1.43 (s, 18H).

3,5-Di-t-butyl Benzoyl Chloride 3,5-Di-t-butyl benzoic acid (9.80 g, 41.81 mmol) was dissolved in SOCl$_2$ (29.9 g, 118.9 mmol) and the light yellow solution was refluxed for three hours under argon with a NaOH trap to neutralize any acidic vapors. The reaction was cooled to room temperature and excess SOCl$_2$ was evaporated under vacuum (liquid N$_2$ trap). The resulting oil was dissolved in dry toluene (100 mL) and the resulting solution was evaporated under vacuum to give 3,5-di-t-butylbenzoyl chloride as a light yellow-green oil (10.5 g, 99% yield).

4-(3,5-Di-t-butylphenyl)-hepta-1,6-diyne4-ol

Magnesium turnings (washed with 1 N HCl, rinsed with distilled water and ether, then dried under vacuum, 3.40 g, 24.30 mmol, 3.4 eq) and HgCl (1.44 g, 6.12 mmol, 0.15 eq) were added under argon to a flame-dried three-necked flask fitted with a condenser, an addition funnel, and a septum. Anhydrous ether (5 mL) was added to the flask via cannula and the flask was cooled to 0° C. A solution of propargyl bromide (18.2 g of 80 wt % solution in toluene, 118.96 mmol bromide, 3.0 eq) was diluted with dry ether (20 mL) and added dropwise via an addition funnel over a period of one hour. The addition rate was maintained such that the temperature remained between 0° and 10° C. to avoid formation of propynyl Grignard. The Grignard reaction started almost immediately and the solvent turned greenish-gray during the addition. The reaction was stirred at 0° C. for three hours. The propargyl Grignard was taken to the next step immediately.

Using this Grignard solution, anhydrous diethyl ether (50 mL) was added to the flask via cannula and the flask was cooled to −78° C. 3,5-di-t-benzoyl chloride (10.31 g, 40.8 mmol, 1 eq) was dissolved in ether (25 mL) and added dropwise via the addition funnel dropwise. The funnel was opened for 10 minutes and closed for 30 minutes to allow the acid chloride to react (3 times). The color slowly changed from gray to yellow with white precipitate during addition of the first fraction. More ether (30 mL) was added and the reaction was stirred for one hours The reaction was then warmed to room temperature and the mixture was quenched with 100 mL water followed by 200 mL 1 N HCl (causing vigorous bubbling), turning the organic layer deep red. The acidic aqueous layer was extracted with ether (3×200 mL), and the organic layers were collected, concentrated, and dried over magnesium sulfate. The red-orange solution was filtered, and the ether was evaporated under vacuum to give 4-(3,5-di-t-butylphenyl)-hepta-1,6-diyne-4-ol as a red oil that was pure by $^1$H NMR spectroscopy (12.4 g, quantitative).

5,6-Bis(trimethylsilyl)-2-(3,5-di-t-butylphenyl)-2-hydroxyl-indane

A solution of C5H5Co(CO) (50 mL, 0.4 mmol) in bis (trimethylsilyl) acetylene (100 mL, excess) was placed in a flame-dried flask under argon. The flask was fitted with a reflux condenser which was capped with a septum. The solution was heated to reflux under a slight pressure of argon. A solution of 4-(3,5-Di-t-butylphenyl)-hepta-1,6-diyne-4-ol (10.9 g, 33.7 mmol) in bis(trimethylsilyl) acetylene (40 mL) was added to the refluxing solution with a syringe pump at a rate of approximately 0.5 mL/hour. The reaction was allowed to reflux for 24 hours after the addition was complete (total of 96 hours). The reaction was cooled to room temperature and the bis(trimethylsilyl) acetylene was vacuum-transferred to another flask for use in future reactions. The remaining brown residue appeared to be pure 5,6-bis(trimethylsilyl)-2-(3,5-di-t-butylphenyl)-2-hydroxyl-indane by $^1$H NMR (15.3 g, 97%).

2-(3,5-Di-t-butylphenyl)-5,6-bis-trimethylsilylindene (Ligand L)

2-(3,5-Di-t-butylphenyl)-5,6-bis-trimethylsilyl-2-hydroxy-indane (15.3 g, 31.1 mmol) was dissolved in 100 mL glacial acetic acid. Toluene (20 mL) was added to help dissolve the alcohol. The solution was cooled to 0° C., and a solution of concentrated sulfuric acid (6.1 g, 62.2 mmol) in glacial acetic acid (30 mL) was added dropwise over a period of 40 minutes. The reaction was stirred at 0° C. for 2 hours. The dark-brown liquid was poured into a 4 L Erlenmeyer flask containing 500 g of ice and 500 mL of water. The mixture was separated into a yellow aqueous layer and a dark brown toluene layer. The aqueous layer was extracted with toluene (3×100 mL). The toluene layers were collected and washed with saturated NaHCO$_3$ solution (2×200 mL), then saturated NaCl solution (1×100 mL). The toluene was then evaporated under reduced pressure to give a very dark oil. $^1$H NMR spectra (CDCl$_3$) showed a mixture of starting material (30%) and a second set of signals (70%) that was consistent with a dehydrated product. The oil was purified by flash chromatography on silica gel. Eluting with hexanes gave a yellow band containing 2-(3,5-di-t-butylphenyl)-5,6-bis-trimethylsilylindene. The remaining black material was eluted using mixtures of methylene chloride in hexanes (1:10, 1:5, 1:1, then 5:1). The only other band was a mixture of dehydrated product and alcohol starting material. The first fraction was evaporated under vacuum to give 2-(3,5di-t-butylphenyl)-5,6-bis-trimethylsilylindene as a yellow powder, which was >95% pure by $^1$HNMR spectroscopy (3.3 g, 6.9 mmol, 22%). $^1$HNMR (CDCl$_3$, 300 MHz) d 7.82 (s, 1H); 7.68 (s, 1H); 7.51 (s, 2H); 7.39 (s, 1H); 7.24 (s, 1H); 3.82 (s, 2H); 0.41 (s, 18H).

2,5-Dichloro-2,5-dimethylhexane

A 2 L three neck round bottom flask fit with an overhead stirrer, thermometer, and nitrogen inlet was charged with 1.2 L concentrated HCl. The HCl was stirred land chilled in an ice/salt bath to 0° C. Gradually, 150 g of 2,5-dimethyl-2,5-hexanediol (Aldrich) was added to the HCl. The reaction mixture was initially a milky white slurry which gradually thickened and the ice bath was removed to allow the reaction to warm to 10 C. The solids were isolated by filtration, dissolved in methylene chloride (500 mL) and washed repeatedly with water until neutral to pH paper. The organics were dried over anhydrous magnesium sulfate and left in the refrigerator overnight. The resulting mixture stripped on the rotary evaporator to yield)of white crystalline 2,5-dichloro-2,5-dimethylhexane (152 g, 94% pure by GC). $^1$HNMR (CDCl$_3$, 500 MHz) δ1.95 (s, 4H); 1.60 (s, 12H).

5,5,8,8-Tetramethyl-5,6,7,8-tetrahydrobenz(f)indane

A flame dried 3 L three neck round bottom flask fit with a magnetic stirrer, condenser, heating mantle, and nitrogen inlet was charged with indane (49 mL, 0.40 mol, Aldrich), anhydrous methylene chloride (800 mL, Aldrich), and 2,5-dichloro-2,5-dimethylhexane. The mixture was heated to reflux and the aluminum chloride (5.65 g, 0.042 mol). was added portionwise while refluxing the reaction. The reaction mixture was quenched in 1 L 5% HCl/ice, the layers separated, and the combined organics washed with water until neutral to pH paper. The organics were then dried over anhydrous magnesium sulfate, stripped of solvent by rotary evaporation and distilled to yield 5,5,8,8-tetramethyl-5,6,7,8-tetrahydrobenz(f)indane (32.1 g, 105–110° C./0.4–0.45 mm Hg, 76–89% pure by GC). $^1$HNMR (CDCl$_3$, 500 MHz) δ7.19 (s, 2H); 2.86 (t, J=7.5 Hz, 4H); 2.04 (p, J=7.5 Hz, 2H); 1.67 (s, 4H); 1.28 (s, 12H).

5,5,8,8-Tetramethyl-5,6,7,8-tetrahydrobenz(f)indan-2-one

A round bottom flask fit with a mechanical stirrer, condenser, thermometer, addition funnel, and nitrogen inlet was charged with 5,5,8,8-tetramethyl-5,6,7,8-tetrahydrobenz(f)indane (43.0 g, 0.0.19 mol) and 84 mL glacial acetic acid and heated to 70° C. While stirring chromate (56.7 g, 0.57 mol, Aldrich) was added slowly maintaining the temperature at about 110° C. After complete addition (30 minutes) the reaction was allowed to cool to room temperature for an additional 2½ hours. The reaction was quenched with 5% HCl/ice and extracted with diethyl ether. The combined ether extracts were washed with water and dried over anhydrous magnesium sulfate. Removal of the solvents by rotary evaporation gave 43.0 g of greenish solids which were washed with chilled acetone to give 16.0 g (98% pure by GC) of solids. The acetone wash was concentrated to give 15.0 g of more solids which were washed with hexane to give 8.7 g (79% pure by GC) of solids. The 16.0 g solids from the acetone wash and 8.7 g solids from the hexane wash were combined to give the crude 5,5,8,8-tetramethyl-5,6,7,8-tetrahydrobenz(f)indan-2one (total of 24.7 g). $^1$HNMR (CDCl$_3$, 500 MHz) 6 7.75 (s, 1H); 7.43 (s, 1H); 3.08 (t, J=3.5 Hz, 2H); 2.66 (t, J=6 Hz, 2H); 1.71 (s, 4H); 1.32 (s, 6H); 1.30 (s, 6H).

5,5,8,8-Tetramethyl-5,6,7,8-tetrahydrobenz(f)indan-2-ol

A 1 L 5 neck round bottom flask fit with magnetic stirrer, condenser, thermometer, and nitrogen inlet was charged with ethanol (anhydrous) and the crude 5,5,8,8-tetramethyl-5,6,7,8-tetrahydrobenz(f)indan-2-one (34.5 g, 0.142 mol, combined from several preparations). The mixture was heated to 30–40° C. and sodium borohydride (11.25 g, 0.298 mol, Aldrich) was added keeping the temperature below 50° C. The reaction was then stirred at 40° C. for 1½ hours and quenched into 5% HCl/ice. The mixture was then extracted with diethyl ether (2×200 mL) and the combined ether extracts washed with water(3×150 mL) and dried over anhydrous sodium sulfate. Removal of the solvents by rotary evaporation yielded the crude 5,5,8,8-tetramethyl-5,6,7,8-tetrahydrobenz(f)indan-2-ol (31.0 g). $^1$HNMR (CDCl$_3$, 500 MHz) δ7.39 (s, 1H); 7.22 (s, 1H); 5.20 (br t, J=6.5 Hz); 3.00 (m, 1H); 2.77 (m, 1H); 2.48 (m, 1H); 1.93 (m, 1H); 1.68 (s, 4H); 1.29 (s, 1H).

5,5,8,8-Tetramethyl-5,6,7,8-tetrahydrobenz(f)indene

A 1 L round bottom flask fit with a magnetic stirrer, condenser, thermometer, and nitrogen inlet was charged with anhydrous toluene (7 mL, Aldrich), the crude 5,5,8,8-tetramethyl-5,6,7,8-tetrahydrobenz(f)indan-2-ol (31.0 g, 0145 mol), pyridine (31.6 mL, 0.39 mol, Aldrich), and p-toluenesulfonyl chloride (30.4 g, 0.16 mol, Aldrich). The mixture was heated to reflux and cooled for GC analysis periodically for a total reflux time of 2 hours. The reaction was then quenched in 5% HCl (250 mL) and extracted into diethyl ether (200 mL). The ether extract was washed with 5% HCl (200 mL), 5% aqueous sodium bicarbonate (until neutral to pH paper), Water (2×200 mL), and dried over anhydrous magnesium chloride. Removal of solvents by rotary evaporation gave 23.0 g of crude product which was purified by chromatography on silica gel (60 g silica gel/hexane eluent) to give 5,5,8,8-tetramethyl-5,6,7,8-tetrahydrobenz(f)indene (17.5 g, 92–99+% pure by GC). $^1$HNMR (CDCl$_3$, 500 MHz) δ7.44 (s, 1H); 7.36 (s, 1H); 6.82 (br d, J=5.5 Hz, 1H); 6.47 (br d, J=5.5 Hz, 1H); 3.51 (s, 2H); 1.70 (s, 4H); 1.32 (s, 12H).

2-(3,5-di-t-butylphenyl)-5,5,8,8 tetramethyl-5,6,7,8-tetrahydrobenz(f)indene (Ligand M)

A 100 mL round bottom flask fit with a magnetic stirrer was charged with 5,5,8,8-tetramethyl-5,6,7,8-tetrahydrobenz(f)indene (4.0 g, 0.018 mol), 3,5-di-t-butyl-bromobenzene (7.0 g, 0.026 mol), tri-o-toylphosphine (2.46 g, 0.0081 mol), triethylamine (4.3 mL, 0.31 mol), and dimethylformamide (60 mL, anhydrous, Aldrich). The solution was degassed, charged with palladium(II) acetate (00876 g, 0.0039 mol) and heated to 60° C. for 93 hours. At that point, after degassing ng again, additional palladium(II) acetate (0.876 g, 0.0039 mol) was added and heated to 60° C. for a total of 161 hours. The reaction mixture was dissolved in 200 mL diethyl ether, washed with 5% HCl (3×100 mL), sodium bicarbonate solution (3×100 mL), water (3×100 mL), and dried over anhydrous magnesium sulfate. The resulting crude oil weighed 11.0 g after rotary evaporation. This material was purified by column chromatography with silica/hexane followed by recrystallization from pentane to yield a fraction (0.8 g) enriched in the desired product. The mother liquid was resubmitted to the coupling conditions. A 50 mL round bottom flask was charged with the mother liquor (7.7 g), tri-o-toylphosphine (2.46 g, 0.0081 mol), triethylamine (4.3 mL, 0.31 mol), and dimethylformamide (35 mL, anhydrous, Aldrich). The solution was degassed, charged with palladium(II) acetate (0.876 g, 0.0039 mol) and heated to 60° C. During heating, periodically more reagents were added such that the totals charged were: tri-o-toylphosphine (3.46 g, 0.011 mol), 1,2-bis(diphenylphosphino)ethane (2.05 g, 0.0051 mol) triethylamine (5.3 mL, 0.38 mol), and dimethylformamide (35 mL, anhydrous, Aldrich), and palladium(II) acetate (3.27 g, 0.0145 mol). The reaction was cooled to room temperature, and worked up as above to yield 11.0 g of crude product. The paste was purified by column chromatography on silica/hexane three times, and the combined most enriched fractions gave 2.3 g which was then purified by preparative HPLC to yield 1.7 g of a semisolid paste. The paste was repeatedly recrystallized from methanol/acetone to yield the pure 2-(3,5-di-t-butylphenyl)-5,5,8,8 tetramethyl-5,6,7,8-tetrahydrobenz(f)indene (0.92 g). $^1$HNMR (CD$_2$Cl$_2$, 500 MHz) δ7.54 (d, J=1.5 Hz, 2H); 7.48 (s, 1H); 7.42 (s, 1H); 7.39 (s, 1H); 7.24 (s, 1H); 3.82 (s, 2H); 1.77 (s, 4H); 1.43 (s, 18H); 1.38 (s, 12H).

Metallocene Preparations

Metallocene compounds containing zirconium or hafnium metal species were prepared from the aforementioned ligands were prepared as described below:

Bis(2-phenylindenyl)hafnium dichloride

Bis(2-phenylindenyl)hafnium dichloride was prepared in the method described in U.S. Pat. No. 5,594,080.

Bis(2-phenylindenyl)zirconium dichloride

Bis(2-phenylindenyl)zirconium dichloride was prepared in the method described in U.S. Pat. No. 5,594,080.

Bis(2-(3,5-bis trifluoromethylphenyl)-indenyl) hafnium dichloride

Bis(2-(3,5-bis trifluoromethylphenyl)-indenyl)hafnium dichloride was prepared by the method described in WO 98/57996.

Bis(2-(3,5-bis trifluoromethylphenyl)-indenyl) zirconium dichloride

Bis(2-(3,5-bis trifluoromethylphenyl)-indenyl)zirconium dichloride was prepared by the method described in WO 98/57996.

Bis(2-(3,5-di-t-butylphenyl)indenyl)hafnium dichloride 2-(3,5-Di-t-butylphenyl)indene (23.3 g, 0.077 mol) and anhydrous diethyl ether (250 mL) were placed in a 1 L three-necked flask under argon. n-Butyl lithium (48 mL of a 1.6 M solution in hexanes, 0.077 mol) was added over a thirty minute period at 0° C. The solution was stirred for an additional two hours. Hafnium tetrachloride (12.2 g, 0.038 mol) was added incrementally over a one-hour period. The mixture was then stirred overnight. The ethereal solution was chilled to −10° C. and the solids were collected by filtration. The solids were taken up in 300 mL of dichloromethane and the residual solids were removed by filtration through celite. The celite was washed with an additional 100 mL of dichloromethane, and the solvents were evaporated to give 23.5 g of bis(2-(3,5-di-t-butylphenyl)indenyl)hafnium dichloride(72% yield).

Bis(2-(3,5-di-t-butylphenyl)indenyl)zirconium dichloride 2-(3,5-Di-t-butylphenyl)indene (13.8 g, 0.045 mol) and anhydrous diethyl ether (250 mL) were placed in a 1 L three-necked flask under argon. n-Butyllithium (28 mL of a 1.6 M solution in hexanes, 0.045 mol) was added over a thirty minute period at 0° C. The solution was stirred for an additional two hours. Zirconium tetrachloride (5.1 g, 0.022 mol) was added incrementally over a one hour period. The mixture then was stirred overnight. The ethereal solution was chilled to −10° C. and the solids were collected. The solids were taken up in 300 mL of dichloromethane and the residual solids were removed by filtration through celite. The celite was washed with an additional 100 mL of dichloromethane and the solvents were evaporated to give 11.2 g of product (64% yield).

Bis(2-(3,5-bis(trimethylsilyl)phenyl)indenyl) hafnium dichloride 2-(3,5-Bis(trimethylsilyl)phenyl)indene (22.3 g, 0.066 mol) and anhydrous diethyl ether (250 mL) were placed in a 1 L three-necked flask under argon. n-Butyllithium (41 mL of a 1.6 M solution in hexanes, 0.066 mol) was added over a thirty minute period at 0° C. The solution was stirred for an additional two hours. Hafnium tetrachloride (10.5 g, 0.033 mol) was added incrementally over a one-hour period. The mixture was then stirred overnight. The ethereal solution was chilled to −10° C. and the solids were collected by filtration. The solids were taken up in 300 mL of dichloromethane and the residual solids were removed by filtration through celite. The celite was washed with an additional 100 mL of dichloromethane and the solvents were evaporated to give 17.3 g of bis(2-(3,5-bis(trimethylsilyl)phenyl)indenyl) hafnium dichloride product (56% yield).

Bis(2-(3,5-bis(trimethylsilyl)phenyl))indenyl) zirconium dichloride 2-(3,5-bis(trimethylsilyl)phenyl)indene (20.5 g, 0.061 mol), and anhydrous diethyl either (250 mL) were placed in a 1 L three-necked flask under argon. n-Butyllithium (38 mL of 1.6 M hexane solution 0.061 mol) was added over a thirty minute period at 0° C. The solution was stirred for an additional two hours. Zirconium tetrachloride (7.0 g, 0.03 mol) was added incrementally over a one hour period. The mixture was then stirred overnight. The ethereal solution was chilled to −10° C. and the solids were collected. The solids were taken up in 300 mL of dichloromethane and the residual solids were removed by filtration through celite. The celite was washed with an additional 100 mL of dichloromethane, and the solvents were evaporated to give 15.6 grams of product (62% yield). $^1$H NMR ($C_6D_6$): δ7.75 (2H, s), 7.62 (1H, s), 6.62 (2H, m), 6.45 (2H, m), 6.41 (2H, s).

Bis(2-(3,5-di-t-butylphenyl)-5,6-bis(trimethylsilyl) indenyl)hafnium dichloride 2-(3,5-Di-t-butylphenyl)-5,6-bis-trimethylsilylindene (1.5 g 3.35 mmol) was dissolved in diethyl ether (100 mL) and cooled to −78° C. Butyllithium (2.1 mL of a 1.6 M solution in hexanes, 3.35 mmol) was added dropwise, causing a slight color change from yellow to yellow orange. The reaction was warmed to room temperature and allowed to stir for 2 hours. The flask was taken into a drybox where HfCl$_4$ (535 mg, 1.67 mmol) was added to the reaction in one portion at room temperature. The reaction was stirred overnight at room temperature. The yellow suspension was cooled to 0° C. and filtered through celite. The celite bed was washed with methylene chloride until the washings ran clear. The yellow methylene chloride solution was evaporated under vacuum to give a yellow powder that was roughly 30% unreacted ligand. Attempts to purify the metallocene with further crystallizations resulted in a loss of yield. The sample was used without further purification (1.22 g total, about 1.0 g of bis(2-(3,5-di-t-butylphenyl)-5,6-bis(trimethylsilyl)indenyl)hafnium dichloride, 0.87 mmol, 52%).

Bis(2-(3,5-di-t-butylphenyl)-5,6-bis(trimethylsilyl) indenyl)zirconium dichloride 2-(3,5-Di-t-butylphenyl)-5,6-bis-trimethylsilylindene (1.5 g, 3.35 mmol) was dissolved in diethyl ether (100 mL) and cooled to −78° C. Butyllithium (2.1 mL of a 1.6 M solution in hexanes, 3.35 mmol) was added dropwise, causing a slight color change from yellow to yellow orange. The reaction was warmed to room temperature and allowed to stir for 2 hours. The flask was taken into a drybox where ZrCl$_4$ (389 mg, 1.67 mmol) was added to the reaction in one portion at room temperature. The reaction was stirred overnight at room temperature The yellow suspension, was cooled to 0° C. and filtered through celite. The celite bed was washed with methylene chloride until the washings ran clear. The yellow methylene chloride solution was evaporated under vacuum to give a yellow powder that was roughly 20% unreacted ligand. The sample was used without further purification (1.25 g total, about 1.1 g bis(2-(3,5-di-t-butylphenyl)-5,6-bis(trimethylsilyl)indenyl)zirconium dichloride, 1.04 mmol, 62%).

General Procedure for the Preparation of Substituted Indenyl Lithium Salts and Preparation of Bis(indenyl)metallocene Dichlorides Using standard high vacuum techniques, the appropriate substituted indene (1.0 equiv.) was dissolved in anhydrous toluene (vacuum distilled from titanocene). The solution was cooled in an ice bath to 4° C. and n-butyllithium (1.2 equiv.) was added. After removing the ice bath and allowing the reaction to warm to room temperature, the reaction was concentrated and anhydrous pentane added to precipitate the product. The solids were washed with anhydrous pentane and dried in vacuo. This product was used for the metallocene preparation without further purification.

Using standard high vacuum techniques, the appropriate substituted indenyl lithium compound (1.0 equiv.) and either hafnium or zirconium tetrachloride (2.0 equiv.) were dissolved in anhydrous toluene (vacuum distilled from titanocene). The reaction was stirred from 4 hours to overnight at room temperature and the volatiles removed in vacuo. The resulting solids were dissolved in anhydrous methylene chloride and filtered through a pad of celite. The methylene chloride solution was concentrated in vacuo and the product dissolved in anhydrous pentane. If the metallocene precipitated during addition or removal of the pentane, it was isolated by filtration and dried in vacuo. If the metallocene was soluble in the pentane/methylene chloride mixture it was isolated by removing the solvent in vacuo. Specific preparations of metallocenes are indicated below:

Bis(2-(4-methylphenyl)-5,6-dimethylindenyl) hafnium dichloride

The ligand was not concentrated during lithiation. The metallocene precipitated with pentane addition. Isolated yield of the metallocene from the substituted indenyl lithium compound was 58%. $^1$HNMR (CDCl$_3$, 500 MHz) δ7.36 (d, $J_{AB}$=8 Hz, 4H); 7.22 (d, $J_{AB}$=8 Hz, 4H); 6.86 (s, 4H); 6.38 (s, 4H); 2.45 (s, 6H); 2.28 (s, 12H).

Bis(2-(4-methylphenyl)-5,6-dimethylindenyl) zirconium dichloride

The ligand was not concentrated during lithiation. The metallocene precipitated with pentane addition. Isolated yield of the metallocene from the substituted indenyl lithium compound was 31%. ¹HNMR (CDCl₃, 500 MHz) δ7.41 (d, JAB=8 Hz, 4H); 7.22 (d, JAB=8 Hz, 4H); 6.61 (s, 4H); 6.54 (s, 4H); 2.45 (s, 6H); 2.24 (s, 12H).

Bis(2-(3,5-di-t-butylphenyl)-5-t-butylindenyl) hafnium dichloride

The lithium salt was isolated by stripping the pentane in vacuo. The metallocene was soluble in pentane/methylene chloride. Isolated yield of the metallocene from the substituted indenyl lithium compound was 41%. ¹HNMR (CDCl₃, 300 MHz) mixture of diastereomers δ7.30–5.52 (m, 16 H); 1.25–0.95 (m, 54H).

Bis(2-(3,5-di-t-butylphenyl)-5-t-butylindenyl) zirconium dichloride

The lithium salt was isolated by stripping the pentane in vacuo. The metallocene was soluble in pentane/methylene chloride. Isolated yield of the metallocene from the substituted indenyl lithium compound was 50%. ¹HNMR (CDCl₃, 300 MHz) mixture of diastereomers δ7.6–5.7 (m, 16H); 1.6–1.1 (m, 54H).

Bis(2-(3,5-di-t-butylphenyl)-5-phenylindenylhafnium dichloride

The lithium salt was isolated by stripping the pentane in vacuo. The metallocene was soluble in pentane/methylene chloride. Isolated yield of the metallocene from the substituted indenyl lithium compound was 65%. ¹HNMR (CDCl3, 300 MHz) mixture of diastereomers δ7.65–6.38 (m, 26H); 1.44 (s, 18H); 1.37 (s, 18H).

Bis(2-(3,5-di-t-butylphenyl)-5-phenylindenylzirconium dichloride

The lithium salt of the metallocene was isolated by stripping the pentane in vacuo. The metallocene was soluble in pentane/methylene chloride. Isolated yield of the metallocene from the substituted indenyl lithium compound was 45%. ¹HNMR (CDCl₃, 300 MHz) mixture of diastereomers δ7.7–6.35 (m, 26H); 1.44 (s, 18H); 1.39 (s, 18H).

Bis(2-(3,5-di-t-butylphenyl)-5-trimethylsilylindenylhafnium dichloride

The lithium salt of the metallocene was isolated by stripping the pentane in vacuo. The metallocene was soluble in pentane/methylene chloride. Isolated yield of the metallocene from the substituted indenyl lithium compound was 64%. ¹HNMR (CDCl₃, 300 MHz) mixture of diastereomers δ7.7–5.95 (m, 16H); 1.6–1.3 (m, 54H).

Bis(2-(3,5-di-t-butylphenyl)-5-trimethylsilylindenylzirconium dichloride

The lithium salt was isolated by stripping the pentane in vacuo. The metallocene was soluble in pentane/methylene chloride. Isolated yield of the metallocene from the substituted indenyl lithium compound was 53%. ¹HNMR (CDCl₃, 300 MHz) mixture of diastereomers δ7.7–5.85 (m, 16H); 1.6–1.3 (m, 54H).

Bis(2-(3,5-di-t-butylphenyl)-5,6-dimethylindenyl) hafnium dichloride

The metallocene was soluble in pentane/methylene chloride. The metallocene was washed with pentane and dried in vacuo. Isolated yield of the metallocene from the substituted indenyl lithium compound was 48%. ¹HNMR (CDCl₃, 300 MHz) δ7.51 (s, 6H); 6.70 (s, 4H); 6.42 (s, 4H); 2.27 (s, 12H); 1.47 (s, 36H).

Bis(2-(3,5-di-t-butylphenyl)-5,6-dimethylindenyl) zirconium dichloride

The metallocene was soluble in pentane/methylene chloride. The metallocene was washed with pentane and dried in vacuo. Isolated yield of the metallocene from the substituted indenyl lithium compound was 68%. ¹HNMR (CDCl₃, 300 MHz) δ7.58 (s, 4H); 7.56 (s, 2H); 6.72 (s, 4H); 6.59 (s, 4H); 2.27 (s, 12H); 1.51 (s, 36H).

Bis(2-(3,5-di-t-butylphenyl)benz(f)indenyl)hafnium dichloride

The lithium salt was isolated by stripping the pentane in vacuo. The metallocene was soluble in pentane/methylene chloride. Isolated yield of the metallocene from the substituted indenyl lithium compound Was 45%. ¹HNMR (CDCl₃, 300 MHz) δ7.59–6.4 (m, 22H); 1.6–0.9 (m, 36H).

Bis(2-(3,5-di-t-butylphenyl)benz(f)indenyl) zirconium dichloride

The lithium salt was isolated by stripping the pentane in vacuo. The metallocene was soluble in pentane/methylene chloride. Isolated yield of the metallocene from the substituted indenyl lithium compound was 55%. ¹HNMR (CDCl₃, 300 MHz) δ7.59–6.5 (m, 22H); 1.65–0.6 (m, 36H).

Bis(2-(3,5-di-t-butylphenyl)-5,5,8,8 tetramethyl-5,6,7,8-tetrahydrobenz(f)indenyl)hafnium dichloride The metallocene was soluble in both methylene chloride and pentane and was isolated by removing all solvent in vacuo. Isolated yield of the metallocene from the substituted indenyl lithium compound was 44%. ¹HNMR (CDCl₃, 300 MHz) δ7.43 (br s, 6H); 7.28 (br s, 4H); 6.20 (br s, 4H); 1.73 (br s, 8H); 1.–01.2 (m, 60H).

Bis(2-(3,5-di-t-butylphenyl)-5,5,8,8 tetramethyl-5,6,7,8tetrahydrobenz(f)indenyl)zirconium dichloride The methylene chloride solution of the metallocene was stripped and the metallocene washed with pentane. Approximately 15% free ligand was seen by NMR and the metallocene used without further purification. Isolated yield, of the metallocene from the substituted indenyl lithium compound was 22% (product contains about 15 wt. % free ligand). ¹HNMR (CDCl₃, 300 MHz) δ7.65–7.00 (m, 10H); 6.30 (s, 4H); 1.65–1.05 (m, 68H).

Polymerizations

A series of propylene polymerization experiments was conducted using metallocene catalyst component together with a MAO co-catalyst. The following polymerization using Metallocene D(Hf) is representative of the conditions used for these experiments:

Polymerization of Propylene Using bis(2-(3,5-tBu$_2$)PhInd)$_2$HfCl$_2$

In an inert atmosphere glove box, a stock solution of bis(2-(3,5-tBu$_2$)PhInd)$_2$HfCl$_2$ metallocene (Metallocene D(Hf)) was prepared by dissolving 4.0 mg (4.68×10⁻³ mmol) in 1 gram of toluene. An aliquot of this solution (0.25 g containing 1.17×10−3 mmol Hf-tBu2) was added to 3.8 grams of heptane and the combined solution then is added to 0.24 grams of DMAO solution (30% Albemarle DMAO in hexanes, 13.1 wt. % Al, giving [Al]/[Hf]=1000). The metallocene/DMAO mixture was stirred in the glove box at room temperature for 30 Minutes. The catalyst solution then was added to a catalyst addition tube attached to a 300 Parr reactor assembly. The entire assembly was removed from the glove box and transferred to a ventilated hood. The Parr reactor was cooled to 17° C. and propylene (100 g) was added. After the reactor was warmed to 47° C., the catalyst addition tube was pressurized with argon such that the pressure in the tube is approximately 100 psi (690 KPa) greater than that in the reactor vessel at 47° C. The contents of the tube then were injected into the reactor and stirred vigorously at 500 rpm. The reaction was allowed to proceed for 30 minutes using internal water cooling and a heating jacket to maintain the reaction temperature at 50° C. After 30 minutes, the vessel was slowly vented to relieve the excess propylene, the polymer was isolated as a white mass and placed in a vacuum oven at 50° C. for 12 hours. Yield of elastomeric polypropylene was 4.5 g (9 kg polymer/g metallocene—hr).

The results of the polymerization experiments are shown in Table 2.

The nomenclature used to identify metallocene compounds used in these Examples is indicated in Table 1.

TABLE 1

| | |
|---|---|
| A(Hf) = | bis(2-phenylindenyl)hafnium dichloride |
| A(Zr) = | bis(2-phenylindenyl)zirconium dichloride |
| B(Hf) = | bis(2-(3,5-bis(trifluoromethyl)phenyl)indenyl)hafnium dichloride |
| B(Zr) = | bis(2-(3,5-bis(trifluoromethyl)phenyl)indenyl)zirconium dichloride |
| C(Hf) = | bis(2-(4-methylphenyl)-5,6-dimethylindenyl)hafnium dichloride |
| C(Zr) = | bis(2-(4-methylphenyl)-5,6-dimethylindenyl)zirconium dichloride |
| D(Hf) = | bis(2-(3,5-di-t-butylphenyl)indenyl)hafnium dichloride |
| D(Zr) = | bis(2-(3,5-di-t-butylphenyl)indenyl)zirconium dichloride |
| E(Hf) = | bis(2-(3,5-bis(trimethylsilyl))indenyl)hafnium dichloride |
| E(Zr) = | bis(2-(3,5-bis(trimethylsilyl))indenyl)zirconium dichloride |
| F(Hf) = | bis(2-(3,5-di-t-butylphenyl)-5-t-butylindenyl)hafnium dichloride |
| F(Zr) = | bis(2-(3,5-di-t-butylphenyl)-5-t-butylindenyl)zirconium dichloride |
| G(Hf) = | bis(2-(3,5-di-t-butylphenyl)-5-trimethylsilylindenyl)hafnium dichloride |
| G(Zr) = | bis(2-(3,5-di-t-butylphenyl)-5-trimethylsilylindenyl)zirconium dichloride |
| H(Hf) = | bis(2-(3,5-di-t-butylphenyl)-5,6-dimethylindenyl)hafnium dichloride |
| H(Zr) = | bis(2-(3,5-di-t-butylphenyl)-5,6-dimethylindenyl)zirconium dichloride |
| J(Hf) = | bis(2-(3,5-di-t-butylphenyl)benz(f)indenyl)hafnium dichloride |
| J(Zr) = | bis(2-(3,5-di-t-butylphenyl)benz(f)indenyl)zirconium dichloride |
| K(Hf) = | bis(2-(4-t-butylphenyl)-5,5,8,8 tetramethyl-5,6,7,8-tetrahydrobenz(f)indenyl) hafnium dichloride |
| K(Zr) = | bis(2-(4-t-butylphenyl)-5,5,8,8 tetramethyl-5,6,7,8-tetrahydrobenz(f)indenyl) zirconium dichloride |
| L(Hf) = | bis(2-(3,5-di-t-butylphenyl)-5,6-bis(trimethylsilyl)indenyl) hafnium dichloride |
| L(Zr) = | bis(2-(3,5-di-t-butylphenyl)-5,6-bis(trimethylsilyl)indenyl) zirconium dichloride |
| M(Hf) = | bis(2-(3,5-di-t-butylphenyl)-5,5,8,8 tetramethyl-5,6,7,8-tetrahydrobenz(f)indenyl)hafnium dichloride |
| M(Zr) = | bis(2-(3,5-di-t-butylphenyl)-5,5,8,8 tetramethyl-5,6,7,8-tetrahydrobenz(f)indenyl)zirconium dichloride |

TABLE 2

| Example (Run) | Temp. (° C.) | Al/M | Metallocene | Activity[1] | MFR | % m4 | Notes[2] |
|---|---|---|---|---|---|---|---|
| C1 | 25 | 1000 | A(Hf) | 2.6 | <0.1 | 11.1 | sMAO |
| C2 | 50 | 1000 | A(Hf) | 6.2 | 39 | 15.5 | sMAO |
| C3 | 25 | 1000 | A(Zr) | 3.6 | 0.9 | 39.4 | sMAO |
| C4 | 50 | 1000 | A(Zr) | 4.9 | >100 | 20.3 | sMAO |
| C5 | 25 | 1000 | B(Zr) | 1.1 | ND[3] | 60 | sMAO Mw 460K |
| C6 | 50 | 1000 | B(Zr) | 3.4 | 15.5 | 54 | sMAO Mw 195K |
| C7 | 25 | 1000 | B(Hf) | 1 | <0.1 | 28 | sMAO Mw 499K |
| C8 | 50 | 1000 | B(Hf) | 4.5 | 2.2 | 31 | sMAO Mw 285K |
| C9 | 50 | 1000 | C(Hf) | 1.1 | ND | 15.1 | |
| C10 | 50 | 1000 | C(Zr) | 4.9 | 25.3 | 13.3 | |
| C11 | 50 | 1000 | J(Hf) | 7 | ND | ND | |
| C12 | 50 | 1000 | J(Zr) | 7.5 | >100 | ND | |
| C13 | 40 | 1000 | J(Zr) | 16 | 67 | ND | |
| C14 | 50 | 1000 | K(Hf) | 7 | 10 | 37.8 | |
| C15 | 50 | 1000 | K(Zr) | 1 | ND | 50.4 | |
| 1 | 23 | 1000 | D(Hf) | 4.5 | 0.1 | 27 | sMAO |
| 2 | 40 | 1000 | D(Hf) | 9 | <0.1 | 26 | sMAO |
| 3 | 50 | 1000 | D(Hf) | 9 | ND | 32 | sMAO |
| 4 | 60 | 1000 | D(Hf) | 5 | ND | 41 | sMAO |
| 5 | 55 | 2000 | D(Hf) | 19.4 | 0.90 | 29 | |
| 6 | 23 | 1000 | D(Zr) | 1.6 | 0.3 | 78 | |
| 7 | 50 | 1000 | D(Zr) | 3 | 6.4 | 71 | sMAO |
| 8 | 23 | 1000 | E(Hf) | 1.5 | ND | 13.6 | sMAO |
| 9 | 50 | 1000 | E(Hf) | 3 | 0.6 | 24 | sMAO |
| 10 | 60 | 1000 | E(Hf) | 3.5 | ND | 31 | sMAO |
| 11 | 50 | 1000 | F(Zr) | 0.23 | ND | 53.1 | Mw = 178K |
| 12 | 50 | 1000 | F(Hf) | 6.3 | ND | 37.1 | Mw = 464K |
| 13 | 50 | 1000 | G(Hf) | 3.6 | ND | 63 | Mw = 500K |
| 14 | 50 | 1000 | G(Zr) | 3.5 | ND | 72 | Mw = 330K |

TABLE 2-continued

| Example (Run) | Temp. (° C.) | Al/M | Metallocene | Activity[1] | MFR | % m4 | Notes[2] |
|---|---|---|---|---|---|---|---|
| 15 | 50 | 1000 | H(Zr) | 0.9 | ND | ND | Mw = 240K |
| 16 | 50 | 1000 | H(Hf) | 24 | 1.3 | 30.1 | Mw = 373K |
| 17 | 50 | 1000 | M(Hf) | 4.6 | 0.2 | 40.7 | |
| 18 | 50 | 1000 | M(Zr) | 0.2 | ND | 53.7 | |
| 19 | 50 | 1000 | L(Hf) | 4.5 | <0.1 | 46 | sMAO |
| 20 | 70 | 1000 | L(Hf) | 5.0 | <1 | 46 | sMAO 30 min run |
| 21 | 80 | 1000 | L(Hf) | 3.2 | 8.9 | 42 | sMAO 30 min run |
| 22 | 50 | 1000 | L(Zr) | 2.4 | 4.1 | 70 | sMAO |
| 23 | 70 | 1000 | L(Zr) | 3.2 | ND | 68 | sMAO |

[1]Kg polymer/g catalyst-hr
[2]Mw measured by gel permeation chromatography (GPC); sMAO = solid MAO prepared from Akzo Type 4A MAO (toluene solution) by drying the solution under vacuum at 60° C. for 24 hours — the resulting fine white powder was used directly.
[3]ND = Not Determined A series of polymerization experiments was performed using Metallocene H(Hf) with different reaction parameters. Unless otherwise noted, runs were performed in 100 grams of propylene at 50° C. for 0.5 hour. using Albemarle DMAO (13.6 wt. % Al) or Akzo PMAO (9.5 wt. % Al) and a constant concentration of heptane (3.8 g) to inject the catalyst solution as described above. The results are shown in Table 3.

TABLE 3

| Example | MAO | [Al]/[Hf] | Activity (Kg/g-hr) | % m4 | MFR |
|---|---|---|---|---|---|
| 23 | DMAO | 1000 | 22 | 28.9 | 0.8 |
| 24 | PMAO | 1000 | 18 | 26.7 | 8.3 |
| 25 | DMAO | 2000 | 38 | 29.1 | 3.0 |
| 26[1] | DMAO | 1000 | 25 | 28.0 | ND |

[1]Polymerization performed at 60° C.

Another series of polymerization experiments was performed using Metallocenes K(Hf) and M(Hf) to demonstrate the effect of hydrogen between a metallocene of this invention (M(Hf)) and a comparison metallocene (K(Hf)). All runs were performed in 100 grams of propylene at 50° C. for 0.5 hour. using Albemarle DMAO (13.6 wt. % Al)) and a constant concentration of heptane (3.8 g) to inject the catalyst solution as described above. The data show that polymer made from the metallocene of this invention has a sufficiently initial low MFR that use of hydrogen results in polymer with acceptable melt flow characteristics, i.e., the polymer does not proceed to very high melt flows with modest amounts of added hydrogen. The results are shown in Table 4.

TABLE 4

| Example (Run) | Metallocene | Hydrogen (mmol $H_2$/mole $C_3^-$) | Activity (Kg/g-hr) | MFR |
|---|---|---|---|---|
| C16-1 | K(Hf) | 0 | 7 | 10 |
| C16-2 | K(Hf) | 0.04 | 18 | >100 |
| C16-3 | K(Hf) | 0.08 | 55 | >100 |
| 27-1 | M(Hf) | 0 | 4.6 | 0.2 |
| 27-2 | M(Hf) | 0.008 | 5 | <1 |
| 27-3 | M(Hf) | 0.016 | 8 | <1 |
| 27-4 | M(Hf) | 0.04 | 10 | ND |

All runs were performed in 100 g propylene at 50° C. for 0.5 hr. using Albemarle DMAO (13.1 wt. % Al) and heptane (3.8 g) to inject the catalyst solution.

What is claimed is:
1. A ligand having a structure comprising:

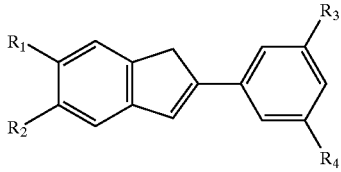

wherein at least $R_3$ or $R_4$ is a bulky substituent and $R_1$ and $R_2$ comprise alkyl, haloalkyl, or alkylsilyl substituents or connected to form a cycloaliphatic ring.

2. The ligand of claim 1 wherein $R_3$ or $R_4$ is based on a tertiary carbon or silicon.

3. The ligand of claim 1 wherein the bulky substituent is t-butyl or trimethylsilyl.

4. The ligand of claim 2 wherein $R_3$ or $R_4$ is t-butyl or trimethylsilyl.

5. The ligand of claim 2 wherein $R_3$ and $R_4$ are t-butyl or trimethylsilyl.

6. The ligand of claim 1 wherein $R_1$, $R_2$, $R_3$ and $R_4$ are t-butyl or trimethylsilyl.

7. The ligand of claim 1 wherein $R_1$ and $R_2$ are trimethylsilyl and $R_3$ and $R_4$ are t-butyl.

8. The ligand of claim 1 wherein $R_1$ and $R_2$ are t-butyl and $R_3$ and $R_4$ are trimethylsilyl.

9. The ligand of claim 1 wherein $R_1$ is trimethylsilyl and $R_3$ and $R_4$ are t-butyl.

10. The ligand of claim 1 where $R_1$ and $R_2$ are connected to form a cycloaliphatic ring.

11. The ligand of claim 1 comprising 2-(3,5-di-t-butylphenyl)indene.

12. The ligand of claim 1 comprising 2-(3,5-bis(trimethylsilyl))indene.

13. The ligand of claim 1 comprising 2-(3,5-di-t-butylphenyl)-5-t-butyl indene.

14. The ligand of claim 1 comprising 2-(3,5-di-t-butylphenyl)-5-trimethylsilylindene.

15. The ligand of claim 1 comprising 2-(3,5-di-t-butylphenyl)-5,6-dimethylindene.

16. The ligand of claim 1 comprising 2-(3,5-di-t-butylphenyl)-5,6-bis-trimethylsilylindene.

17. The ligand of claim 1 comprising 2-(3,5-di-t-butylphenyl)-5,5,8,8 tetramethyl-5,6,7,8-tetrahydrobenz(f) indene.

18. A bis metallocene catalyst component in which a Group 4 transition metal is coordinated with a ligand comprising the structure:

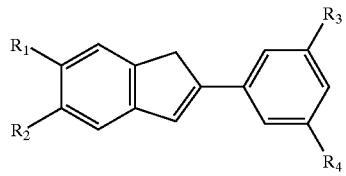

wherein at least $R_3$ or $R_4$ is a bulky substituent and $R_1$ and $R_2$ comprise alkyl, haloalkyl, or alkylsilyl substituents or connected to form a cycloaliphatic ring.

19. The metallocene catalyst component of claim 18 wherein the transition metal is zirconium or hafnium.

20. The metallocene catalyst component of claim 18 wherein wherein the bulky substituent on the ligand is t-butyl or trimethylsilyl.

21. The metallocene catalyst component of claim 18 wherein wherein $R_1$, $R_2$, $R_3$ and $R_4$ on the ligand are t-butyl or trimethylsilyl.

22. The metallocene catalyst component of claim 18 wherein the transition metal is hafnium.

23. The metallocene catalyst component of claim 18 comprising bis(2-(3,5-di-t-butylphenyl)indenyl)hafnium dichloride; bis(2-(3,5-di-t-butylphenyl)indenyl) zirconium dichloride; bis(2-(3,5-bis(trimethylsilyl))indenyl)hafnium dichloride; bis(2-(3,5-bis(trimethylsilyl))indenyl)zirconium dichloride; bis(2-(3,5-di-t-butylphenyl)-5-t-butylindenyl) hafnium dichloride; bis(2-(3,5-di-t-butylphenyl)-5-t-butylindenyl)zirconium dichloride; bis(2-(3,5-di-t-butylphenyl)-5-trimethylsilylindenyl)hafnium dichloride; bis(2-(3,5-di-t-butylphenyl)-5-trimethylsilylindenyl) zirconium dichloride; bis(2-(3,5-di-t-butylphenyl)-5,6-dimethylindenyl)hafnium dichloride; bis(2-(3,5-di-t-butylphenyl)-5,6-dimethylindenyl)zirconium dichloride; bis (2-(3,5-di-t-butylphenyl)-5,6-bis(trimethylsilyl)indenyl) hafnium dichloride; bis(2-(3,5-di-t-butylphenyl)-5,6-bis(trimethylsilyl)indenyl)zirconium dichloride; bis(2-(3,5-di-t-butylphenyl)-5,5,8,8 tetramethyl-5,6,7,8-tetrahydrobenz(f) indenyl)hafnium dichloride; or bis(2-(3,5-di-t-butylphenyl)-5,5,8,8 tetramethyl-5,6,7,8-tetrahydrobenz(f)indenyl) zirconium dichloride.

24. The metallocene catalyst component of claim 18 comprising bis(2-(3,5-di-t-butylphenyl)indenyl)hafnium dichloride; bis(2-(3,5-bis(trimethylsilyl))indenyl)hafnium dichloride; bis(2-(3,5-di-t-butylphenyl)-5-t-butylindenyl) hafnium dichloride; bis(2-(3,5-di-t-butylphenyl)-5-trimethylsilylindenyl)hafnium dichloride; bis(2-(3,5-di-t-butylphenyl)-5,6-dimethylindenyl)hafnium dichloride; bis (2-(3,5-di-t-butylphenyl)-5,6-bis(trimethylsilyl)indenyl) hafnium dichloride; or bis(2-(3,5-di-t-butylphenyl)-5,5,8,8 tetramethyl-5,6,7,8-tetrahydrobenz(f)indenyl)hafnium dichloride.

25. The metallocene catalyst component of claim 18 comprising bis(2-(3,5-di-t-butylphenyl)indenyl)hafnium dichloride; bis(2-(3,5-bis(trimethylsilyl))indenyl)hafnium dichloride; bis(2-(3,5-di-t-butylphenyl)-5,6-dimethylindenyl)hafnium dichloride; or bis(2-(3,5-di-t-butylphenyl)-5,6-bis(trimethylsilyl)indenyl)hafnium dichloride.

26. A process to polymerize an olefin comprising contacting propylene, ethylene, or a mixture thereof with a metallocene catalyst component of claim 18 and a compatible anionic cocatalyst under polymerization conditions.

* * * * *

UNITED STATES PATENT AND TRADEMARK OFFICE
CERTIFICATE OF CORRECTION

PATENT NO. : 6,479,424 B1
DATED : November 12, 2002
INVENTOR(S) : Andreas B. Ernst et al.

It is certified that error appears in the above-identified patent and that said Letters Patent is hereby corrected as shown below:

Column 1,
Line 30, "ligands that ore formed" should read -- ligands that are formed --

Column 4,
Line 15, "$(PhNMe_2H)^+B(C_6F_5)^+,$" should read -- $(PhNMe_2H)^+B(C_6F_5)_4^-,$ --
Line 37, "chloride, chlorobenzene fluorobenzone," should read
-- chloride, chlorobenzene, fluorobenzene, --

Column 7,
Line 43, "2,26 (s, 3H);" should read -- 2.26 (s, 3H); --

Column 8,
Line 57, "$^{nHNMR\ (CD}_2Cl_2$, 500 MHz)" should read
-- $^1HNMR\ (CD_2Cl_2$, 500 MHz) --

Column 11,
Line 44, "6-t-butyl+1-indanol" should read -- 6-t-butyl-1-indanol --

Column 12,
Line 12, "column chromatography oh" should read -- column chromatography on --

Column 14,
Line 52, "(10.2 2 g, 0.036 mol)" should read -- (10.2 g, 0.036 mol) --

Column 15,
Line 56, "and yielded [ u]pon evaporation of" should read -- and yielded, upon evaporation of --

Column 16,
Line 33, "($CDCl_3$, 300 MHz δ 7.95-7.77" should read -- ($CDCl_3$, 300 MHz) δ 7.95-7.77 --

Column 17,
Line 8, "for one hours The reaction" should read -- for one hour. The reaction --

Column 18,
Lines 4 and 5, "3.82 (s, 2H); 0.41 (s, 18H)." should read
-- 3.82 (s, 2H); 1.39 (s, 18H); 0.41 (s, 18H). --
Line 10, "stirred land chilled in an" should read -- stirred and chilled in an --
Line 65, "2one (total of 24.7 g)." should read -- 2-one (total of 24.7 g). --

UNITED STATES PATENT AND TRADEMARK OFFICE
CERTIFICATE OF CORRECTION

PATENT NO. : 6,479,424 B1
DATED : November 12, 2002
INVENTOR(S) : Andreas B. Ernst et al.

It is certified that error appears in the above-identified patent and that said Letters Patent is hereby corrected as shown below:

Column 19,
Line 27, "0145 mol), pyridine" should read -- 0.145 mol), pyridine --
Line 53, "(00876 g, 0.0039 mol)" should read -- (0.876 g, 0.0039 mol) --
Line 54, "point, after degassing ng again," should read -- point, after degassing again, --

Column 22,
Line 18, "temperature The yellow suspension, was" should read -- temperature. The yellow suspension was --

Signed and Sealed this

Fifteenth Day of July, 2003

JAMES E. ROGAN
*Director of the United States Patent and Trademark Office*